(12) United States Patent
Arts et al.

(10) Patent No.: US 7,955,332 B2
(45) Date of Patent: Jun. 7, 2011

(54) MECHANISM FOR DIVIDING TISSUE IN A HEMOSTAT-STYLE INSTRUMENT

(75) Inventors: Gene H. Arts, Berthoud, CO (US); Gary M. Couture, Longmont, CO (US); Kristin D. Johnson, Louisville, CO (US); Michael C. Moses, Boulder, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 598 days.

(21) Appl. No.: 11/232,174

(22) Filed: Sep. 21, 2005

(65) Prior Publication Data
US 2006/0079891 A1      Apr. 13, 2006

Related U.S. Application Data

(60) Provisional application No. 60/616,968, filed on Oct. 8, 2004.

(51) Int. Cl.
*A61B 18/14* (2006.01)
*A61B 17/28* (2006.01)

(52) U.S. Cl. .............................. 606/51; 606/52; 606/174
(58) Field of Classification Search .................. 606/174, 606/51–52; 30/175
See application file for complete search history.

(56) References Cited

U.S. PATENT DOCUMENTS

| | | |
|---|---|---|
| 371,664 A | 10/1887 | Brannan et al. |
| 702,472 A | 6/1902 | Pignolet |
| 728,883 A | 5/1903 | Downes |
| 1,586,645 A | 6/1926 | Bierman |
| 1,813,902 A | 7/1931 | Bovie |
| 1,822,330 A | 9/1931 | Ainslie |
| 1,852,542 A | 4/1932 | Sovatkin |
| 2,002,594 A | 5/1935 | Wappler et al. |
| 2,011,169 A | 8/1935 | Wappler |
| 2,031,682 A | 2/1936 | Wappler et al. |
| 2,054,149 A | 9/1936 | Wappler |
| 2,176,479 A | 10/1939 | Willis |
| 2,305,156 A | 4/1941 | Grubel |
| 2,279,753 A | 4/1942 | Knopp |

(Continued)

FOREIGN PATENT DOCUMENTS

CA           2104423           2/1994

(Continued)

OTHER PUBLICATIONS

Int'l Search Report EP 04 752343.6 dated Jul. 20, 2007.

(Continued)

*Primary Examiner* — Michael Peffley
*Assistant Examiner* — Samantha Good

(57) ABSTRACT

Open electrosurgical forceps for sealing tissue are provided which include first and second shaft portions pivotably associated with one another. Each shaft portion has a jaw member disposed at a distal end thereof. Each of the jaw members includes an electrically conductive sealing surface adapted to communicate electrosurgical energy through tissue held therebetween and a slot formed through the sealing surface thereof. The forceps includes a cutting mechanism operatively associated with the first and second jaw members. The cutting mechanism includes a cutting element disposed within the slot of the at least one jaw member, the cutting element being movable from a first position wherein the cutting element is retracted within the at least one jaw member and a second position in which the cutting element at least partially projects from a sealing surface of the at least one jaw member.

13 Claims, 14 Drawing Sheets

U.S. PATENT DOCUMENTS

| | | | |
|---|---|---|---|
| 2,327,353 A | 8/1943 | Karle | |
| 2,632,661 A | 8/1948 | Cristofv | |
| 2,668,538 A | 2/1954 | Baker | |
| 2,796,065 A | 6/1957 | Kapp | |
| 3,073,311 A | 1/1963 | Tibbs et al. | |
| 3,459,187 A | 3/1967 | Pallotta | |
| 3,372,288 A | 3/1968 | Wigington | |
| 3,643,663 A | 2/1972 | Sutter | |
| 3,648,001 A | 3/1972 | Anderson et al. | |
| 3,651,811 A | 3/1972 | Hildebrandt et al. | |
| 3,678,229 A | 7/1972 | Osika | |
| 3,720,896 A | 3/1973 | Beierlein | |
| 3,763,726 A | 10/1973 | Hildebrand | |
| 3,779,918 A | 12/1973 | Ikeda et al. | |
| 3,801,766 A | 4/1974 | Morrison, Jr. | |
| 3,862,630 A | 1/1975 | Balamuth | |
| 3,863,339 A | 2/1975 | Reaney et al. | |
| 3,866,610 A | 2/1975 | Kletschka | |
| 3,911,766 A | 10/1975 | Fridolph et al. | |
| 3,920,021 A | 11/1975 | Hiltebrandt | |
| 3,921,641 A | 11/1975 | Hulka | |
| 3,938,527 A | 2/1976 | Rioux et al. | |
| 3,952,749 A | 4/1976 | Fridolph et al. | |
| 3,970,088 A | 7/1976 | Morrison | |
| 3,987,795 A | 10/1976 | Morrison | |
| 4,005,714 A | 2/1977 | Hiltebrandt | |
| 4,016,881 A | 4/1977 | Rioux et al. | |
| 4,041,952 A | 8/1977 | Morrison, Jr. et al. | |
| 4,043,342 A | 8/1977 | Morrison, Jr. | |
| 4,074,718 A | 2/1978 | Morrison, Jr. | |
| 4,076,028 A | 2/1978 | Simmons | |
| 4,080,820 A | 3/1978 | Allen | |
| 4,088,134 A | 5/1978 | Mazzariello | |
| 4,112,950 A | 9/1978 | Pike | |
| 4,127,222 A | 11/1978 | Adams | |
| 4,128,099 A | 12/1978 | Bauer | |
| 4,165,746 A | 8/1979 | Burgin | |
| 4,187,420 A | 2/1980 | Piber | |
| 4,233,734 A | 11/1980 | Bies | |
| 4,236,470 A | 12/1980 | Stenson | |
| 4,300,564 A | 11/1981 | Furihata | |
| 4,311,145 A | 1/1982 | Esty et al. | |
| D263,020 S | 2/1982 | Rau, III | |
| 4,370,980 A | 2/1983 | Lottick | |
| 4,375,218 A | 3/1983 | DiGeronimo | |
| 4,416,276 A | 11/1983 | Newton et al. | |
| 4,418,692 A | 12/1983 | Guay | |
| 4,443,935 A | 4/1984 | Zamba et al. | |
| 4,452,246 A | 6/1984 | Bader et al. | |
| 4,470,786 A | 9/1984 | Sano et al. | |
| 4,492,231 A | 1/1985 | Auth | |
| 4,493,320 A | 1/1985 | Treat | |
| 4,503,855 A | 3/1985 | Maslanka | |
| 4,506,669 A | 3/1985 | Blake, III | |
| 4,509,518 A | 4/1985 | McGarry et al. | |
| 4,552,143 A | 11/1985 | Lottick | |
| 4,574,804 A | 3/1986 | Kurwa | |
| 4,597,379 A | 7/1986 | Kihn et al. | |
| 4,600,007 A | 7/1986 | Lahodny et al. | |
| 4,624,254 A | 11/1986 | McGarry et al. | |
| 4,655,215 A | 4/1987 | Pike | |
| 4,655,216 A * | 4/1987 | Tischer | 606/51 |
| 4,657,016 A | 4/1987 | Garito et al. | |
| 4,662,372 A | 5/1987 | Sharkany et al. | |
| 4,671,274 A | 6/1987 | Sorochenko | |
| 4,685,459 A | 8/1987 | Xoch et al. | |
| 4,733,662 A | 3/1988 | DeSatnick et al. | |
| D295,893 S | 5/1988 | Sharkany et al. | |
| D295,894 S | 5/1988 | Sharkany et al. | |
| 4,754,892 A | 7/1988 | Retief | |
| 4,763,669 A | 8/1988 | Jaeger | |
| 4,827,929 A | 5/1989 | Hodge | |
| 4,829,313 A | 5/1989 | Taggart | |
| 4,846,171 A | 7/1989 | Kauphusman et al. | |
| 4,887,612 A | 12/1989 | Esser et al. | |
| 4,938,761 A | 7/1990 | Ensslin | |
| 4,947,009 A | 8/1990 | Osika et al. | |
| 4,985,030 A | 1/1991 | Melzer et al. | |
| 5,007,908 A | 4/1991 | Rydell | |
| 5,026,370 A | 6/1991 | Lottick | |
| 5,026,371 A | 6/1991 | Rydell et al. | |
| 5,035,695 A | 7/1991 | Weber, Jr. et al. | |
| 5,037,433 A | 8/1991 | Wilk et al. | |
| 5,042,707 A | 8/1991 | Taheri | |
| 5,047,046 A | 9/1991 | Bodoia | |
| 5,078,716 A | 1/1992 | Doll | |
| 5,084,057 A | 1/1992 | Green et al. | |
| 5,085,659 A | 2/1992 | Rydell | |
| 5,099,840 A | 3/1992 | Goble et al. | |
| 5,100,430 A | 3/1992 | Avellanet et al. | |
| 5,108,392 A | 4/1992 | Spingler | |
| 5,112,343 A | 5/1992 | Thornton | |
| 5,116,332 A | 5/1992 | Lottick | |
| 5,147,357 A | 9/1992 | Rose et al. | |
| 5,151,102 A | 9/1992 | Xamiyama et al. | |
| 5,151,978 A | 9/1992 | Bronikowski et al. | |
| 5,176,695 A | 1/1993 | Dulebohn | |
| 5,190,541 A | 3/1993 | Abele et al. | |
| 5,196,009 A | 3/1993 | Kirwan, Jr. | |
| 5,197,964 A | 3/1993 | Parins | |
| 5,209,747 A | 5/1993 | Knoepfler | |
| 5,211,655 A | 5/1993 | Hasson | |
| 5,215,101 A | 6/1993 | Jacobs et al. | |
| 5,217,457 A | 6/1993 | Delahuerga et al. | |
| 5,217,458 A | 6/1993 | Parins | |
| 5,217,460 A | 6/1993 | Knoepfler | |
| 5,219,354 A | 6/1993 | Choudhury et al. | |
| 5,244,462 A | 9/1993 | Delahuerga et al. | |
| 5,250,047 A | 10/1993 | Rydell | |
| 5,250,063 A | 10/1993 | Abidin et al. | |
| 5,258,001 A | 11/1993 | Corman | |
| 5,258,006 A | 11/1993 | Rydell et al. | |
| 5,261,918 A | 11/1993 | Phillips et al. | |
| 5,275,615 A | 1/1994 | Rose | |
| 5,277,201 A | 1/1994 | Stern | |
| 5,282,799 A | 2/1994 | Rydell | |
| 5,282,800 A | 2/1994 | Foshee et al. | |
| 5,282,826 A | 2/1994 | Quadri | |
| 5,290,286 A | 3/1994 | Parins | |
| 5,300,082 A | 4/1994 | Sharpe et al. | |
| 5,304,203 A | 4/1994 | El-Mallawany et al. | |
| 5,308,353 A | 5/1994 | Beurrier | |
| 5,308,357 A | 5/1994 | Lichtman | |
| 5,313,027 A | 5/1994 | Inoue et al. | |
| 5,314,445 A | 5/1994 | Degwitz et al. | |
| 5,318,589 A | 6/1994 | Lichtman | |
| 5,324,289 A | 6/1994 | Eggers | |
| D348,930 S | 7/1994 | Olson | |
| 5,326,806 A | 7/1994 | Yokoshima et al. | |
| 5,330,471 A | 7/1994 | Eggers | |
| 5,330,502 A | 7/1994 | Hassler et al. | |
| 5,334,183 A | 8/1994 | Wuchinich | |
| 5,334,215 A | 8/1994 | Chen | |
| 5,336,220 A | 8/1994 | Ryan et al. | |
| 5,336,221 A | 8/1994 | Anderson | |
| 5,342,359 A | 8/1994 | Rydell | |
| 5,342,381 A | 8/1994 | Tidemand | |
| 5,342,393 A | 8/1994 | Stack | |
| 5,344,424 A | 9/1994 | Roberts et al. | |
| 5,350,391 A | 9/1994 | Iacovelli | |
| 5,352,222 A | 10/1994 | Rydell | |
| 5,354,271 A | 10/1994 | Voda | |
| 5,356,408 A | 10/1994 | Rydell | |
| 5,366,477 A | 11/1994 | LeMarie, III et al. | |
| 5,368,600 A | 11/1994 | Failla et al. | |
| 5,374,277 A | 12/1994 | Hassler | |
| 5,376,089 A | 12/1994 | Smith | |
| 5,383,875 A | 1/1995 | Bays et al. | |
| 5,383,897 A | 1/1995 | Wholey | |
| 5,389,098 A | 2/1995 | Tsuruta et al. | |
| 5,389,103 A | 2/1995 | Melzer et al. | |
| 5,389,104 A | 2/1995 | Hahnen et al. | |
| 5,391,166 A | 2/1995 | Eggers | |
| 5,391,183 A | 2/1995 | Janzen et al. | |
| 5,396,900 A | 3/1995 | Slater et al. | |
| 5,403,312 A | 4/1995 | Yates et al. | |
| 5,403,342 A | 4/1995 | Tovey et al. | |

| | | | | | | |
|---|---|---|---|---|---|---|
| 5,405,344 | A | 4/1995 | Williamson et al. | 5,603,711 A | 2/1997 | Parins et al. |
| 5,409,763 | A | 4/1995 | Serizawa et al. | 5,603,723 A | 2/1997 | Aranyi et al. |
| 5,411,519 | A | 5/1995 | Tovey et al. | 5,611,798 A | 3/1997 | Eggers |
| 5,411,520 | A | 5/1995 | Nash et al. | 5,611,808 A | 3/1997 | Hossain et al. |
| 5,413,571 | A | 5/1995 | Katsaros et al. | 5,611,813 A | 3/1997 | Lichtman |
| 5,415,656 | A | 5/1995 | Tihon et al. | 5,620,415 A | 4/1997 | Lucey et al. |
| 5,415,657 | A | 5/1995 | Taymor-Luria | 5,620,453 A | 4/1997 | Nallakrishnan |
| 5,422,567 | A | 6/1995 | Matsunaga | 5,620,459 A | 4/1997 | Lichtman |
| 5,423,810 | A | 6/1995 | Goble et al. | 5,624,452 A | 4/1997 | Yates |
| 5,425,690 | A | 6/1995 | Chang | 5,626,578 A | 5/1997 | Tihon |
| 5,425,739 | A | 6/1995 | Jessen | 5,626,609 A | 5/1997 | Zvenyatsky et al. |
| 5,429,616 | A | 7/1995 | Schaffer | 5,630,833 A | 5/1997 | Katsaros et al. |
| 5,431,672 | A | 7/1995 | Cote et al. | 5,637,110 A | 6/1997 | Pennybacker et al. |
| 5,431,674 | A | 7/1995 | Basile et al. | 5,638,003 A | 6/1997 | Hall |
| 5,437,292 | A | 8/1995 | Kipshidze et al. | 5,643,294 A | 7/1997 | Tovey et al. |
| 5,438,302 | A | 8/1995 | Goble | 5,647,869 A | 7/1997 | Goble et al. |
| 5,439,478 | A | 8/1995 | Palmer | 5,647,871 A | 7/1997 | Levine et al. |
| 5,441,517 | A | 8/1995 | Kensey et al. | 5,649,959 A | 7/1997 | Hannam et al. |
| 5,443,463 | A | 8/1995 | Stern et al. | 5,655,650 A | 8/1997 | Naitou |
| 5,443,464 | A | 8/1995 | Russell et al. | 5,658,281 A | 8/1997 | Heard |
| 5,443,480 | A | 8/1995 | Jacobs et al. | D384,413 S | 9/1997 | Zlock et al. |
| 5,445,638 | A | 8/1995 | Rydell et al. | 5,662,667 A | 9/1997 | Knodel |
| 5,445,658 | A | 8/1995 | Durrfeld et al. | 5,665,100 A | 9/1997 | Yoon |
| 5,449,480 | A | 9/1995 | Kuriya et al. | 5,667,526 A | 9/1997 | Levin |
| 5,451,224 | A | 9/1995 | Goble et al. | 5,674,220 A | 10/1997 | Fox et al. |
| 5,454,823 | A | 10/1995 | Richardson et al. | 5,674,229 A | 10/1997 | Tovey et al. |
| 5,454,827 | A | 10/1995 | Aust et al. | 5,681,282 A | 10/1997 | Eggers et al. |
| 5,456,684 | A | 10/1995 | Schmidt et al. | 5,688,270 A | 11/1997 | Yates et al. |
| 5,458,598 | A | 10/1995 | Feinberg et al. | 5,690,652 A | 11/1997 | Wurster et al. |
| 5,460,629 | A | 10/1995 | Shlain et al. | 5,690,653 A | 11/1997 | Richardson et al. |
| 5,461,765 | A | 10/1995 | Linden et al. | 5,693,051 A | 12/1997 | Schulze et al. |
| 5,462,546 | A | 10/1995 | Rydell | 5,693,920 A | 12/1997 | Maeda |
| 5,472,442 | A | 12/1995 | Klicek | 5,695,522 A | 12/1997 | LeMaire, III et al. |
| 5,472,443 | A | 12/1995 | Cordis et al. | 5,700,261 A | 12/1997 | Brinkerhoff |
| 5,478,351 | A | 12/1995 | Meade et al. | 5,700,270 A | 12/1997 | Peyser et al. |
| 5,480,406 | A | 1/1996 | Nolan et al. | 5,702,390 A | 12/1997 | Austin et al. |
| 5,480,409 | A | 1/1996 | Riza | 5,707,369 A | 1/1998 | Vaitekunas et al. |
| 5,484,436 | A | 1/1996 | Eggers et al. | 5,709,680 A | 1/1998 | Yates et al. |
| 5,496,312 | A | 3/1996 | Klicek | 5,716,366 A | 2/1998 | Yates |
| 5,496,317 | A | 3/1996 | Goble et al. | 5,720,744 A | 2/1998 | Eggleston et al. |
| 5,496,347 | A | 3/1996 | Hashiguchi et al. | 5,722,421 A | 3/1998 | Francese et al. |
| 5,499,997 | A | 3/1996 | Sharpe et al. | 5,725,536 A | 3/1998 | Oberlin et al. |
| 5,509,922 | A | 4/1996 | Aranyi et al. | 5,727,428 A | 3/1998 | LeMaire, III et al. |
| 5,514,134 | A | 5/1996 | Rydell et al. | 5,735,848 A | 4/1998 | Yates et al. |
| 5,527,313 | A | 6/1996 | Scott et al. | 5,743,906 A | 4/1998 | Parins et al. |
| 5,528,833 | A | 6/1996 | Sakuma | 5,752,973 A | 5/1998 | Kieturakis |
| 5,529,067 | A | 6/1996 | Larsen et al. | 5,755,717 A | 5/1998 | Yates et al. |
| 5,531,744 | A | 7/1996 | Nardella et al. | 5,759,188 A | 6/1998 | Yoon |
| 5,536,251 | A | 7/1996 | Evard et al. | 5,766,130 A | 6/1998 | Selmonosky |
| 5,540,684 | A | 7/1996 | Hassler, Jr. | 5,766,166 A | 6/1998 | Hooven |
| 5,540,685 | A | 7/1996 | Parins et al. | 5,766,170 A | 6/1998 | Eggers |
| 5,540,706 | A | 7/1996 | Aust et al. | 5,766,196 A | 6/1998 | Griffiths |
| 5,540,715 | A | 7/1996 | Katsaros et al. | 5,769,849 A | 6/1998 | Eggers |
| 5,542,945 | A | 8/1996 | Fritzsch | 5,772,655 A | 6/1998 | Bauer et al. |
| 5,558,671 | A | 9/1996 | Yates | 5,772,670 A | 6/1998 | Brosa |
| 5,558,672 | A | 9/1996 | Edwards et al. | 5,776,128 A | 7/1998 | Eggers |
| 5,562,619 | A | 10/1996 | Mirarchi et al. | 5,776,130 A | 7/1998 | Buysse et al. |
| 5,562,699 | A | 10/1996 | Heimberger et al. | 5,779,646 A | 7/1998 | Koblish et al. |
| 5,562,720 | A | 10/1996 | Stern et al. | 5,779,701 A | 7/1998 | McBrayer et al. |
| 5,564,615 | A | 10/1996 | Bishop et al. | H1745 H | 8/1998 | Paraschac |
| 5,569,241 | A | 10/1996 | Edwardds | 5,792,137 A | 8/1998 | Carr et al. |
| 5,569,243 | A | 10/1996 | Kortenbach et al. | 5,792,165 A | 8/1998 | Klieman et al. |
| 5,571,100 | A | 11/1996 | Goble et al. | 5,792,177 A | 8/1998 | Kaseda |
| 5,573,424 | A | 11/1996 | Poppe | 5,797,537 A | 8/1998 | Oberlin et al. |
| 5,573,534 | A | 11/1996 | Stone | 5,797,927 A | 8/1998 | Yoon |
| 5,573,535 | A | 11/1996 | Viklund | 5,797,938 A | 8/1998 | Paraschac et al. |
| 5,575,799 | A | 11/1996 | Bolanos et al. | 5,797,941 A | 8/1998 | Schulze et al. |
| 5,575,805 | A | 11/1996 | Li | 5,797,958 A | 8/1998 | Yoon |
| 5,578,052 | A | 11/1996 | Koros et al. | 5,800,449 A | 9/1998 | Wales |
| 5,579,781 | A | 12/1996 | Cooke | 5,807,393 A | 9/1998 | Williamson, IV et al. |
| 5,582,611 | A | 12/1996 | Tsuruta et al. | 5,810,764 A | 9/1998 | Eggers et al. |
| 5,582,617 | A | 12/1996 | Klieman et al. | 5,810,805 A | 9/1998 | Sutcu et al. |
| 5,585,896 | A | 12/1996 | Yamazaki et al. | 5,810,808 A | 9/1998 | Eggers |
| 5,590,570 | A | 1/1997 | LeMaire, III et al. | 5,810,811 A | 9/1998 | Yates et al. |
| 5,591,181 | A | 1/1997 | Stone et al. | 5,810,877 A | 9/1998 | Roth et al. |
| 5,597,107 | A | 1/1997 | Knodel et al. | 5,814,043 A | 9/1998 | Shapeton |
| 5,601,224 | A | 2/1997 | Bishop et al. | 5,814,054 A | 9/1998 | Kortenbach et al. |
| 5,601,601 | A | 2/1997 | Tal et al. | 5,817,083 A | 10/1998 | Shemesh et al. |
| 5,601,641 | A | 2/1997 | Stephens | 5,817,119 A | 10/1998 | Klieman et al. |

| Patent | Date | Inventor |
|---|---|---|
| 5,820,630 A | 10/1998 | Lind |
| 5,824,978 A | 10/1998 | Karasik et al. |
| 5,827,271 A | 10/1998 | Buysse et al. |
| 5,827,279 A | 10/1998 | Hughett et al. |
| 5,827,281 A | 10/1998 | Levin |
| 5,827,323 A | 10/1998 | Klieman et al. |
| 5,827,548 A | 10/1998 | Lavallee et al. |
| 5,833,690 A | 11/1998 | Yates et al. |
| 5,843,080 A | 12/1998 | Fleenor et al. |
| 5,849,022 A | 12/1998 | Sakashita et al. |
| 5,853,412 A | 12/1998 | Mayenberger |
| 5,859,527 A | 1/1999 | Cook |
| 5,860,976 A | 1/1999 | Billings et al. |
| 5,876,401 A | 3/1999 | Schulze et al. |
| 5,876,412 A | 3/1999 | Piraka |
| 5,882,567 A | 3/1999 | Cavallaro et al. |
| 5,891,141 A | 4/1999 | Rydell |
| 5,891,142 A | 4/1999 | Eggers et al. |
| 5,893,863 A | 4/1999 | Yoon |
| 5,893,875 A | 4/1999 | O'Connor et al. |
| 5,893,877 A | 4/1999 | Gampp, Jr. et al. |
| 5,897,563 A | 4/1999 | Yoon et al. |
| 5,902,301 A | 5/1999 | Olig |
| 5,906,630 A | 5/1999 | Anderhub et al. |
| 5,908,420 A | 6/1999 | Parins et al. |
| 5,908,432 A | 6/1999 | Pan |
| 5,911,719 A | 6/1999 | Eggers |
| 5,913,874 A | 6/1999 | Berns et al. |
| 5,921,916 A | 7/1999 | Aeikens et al. |
| 5,921,984 A | 7/1999 | Sutcu et al. |
| 5,925,043 A | 7/1999 | Kumar et al. |
| 5,928,136 A | 7/1999 | Barry |
| 5,935,126 A | 8/1999 | Riza |
| 5,941,869 A | 8/1999 | Patterson et al. |
| 5,944,718 A | 8/1999 | Austin et al. |
| 5,951,546 A | 9/1999 | Lorentzen |
| 5,951,549 A | 9/1999 | Richardson et al. |
| 5,954,720 A | 9/1999 | Wilson et al. |
| 5,954,731 A | 9/1999 | Yoon |
| 5,954,733 A | 9/1999 | Yoon |
| 5,957,923 A | 9/1999 | Hahnen et al. |
| 5,957,937 A | 9/1999 | Yoon |
| 5,960,544 A | 10/1999 | Beyers |
| 5,961,514 A | 10/1999 | Long et al. |
| 5,964,758 A | 10/1999 | Dresden |
| 5,976,132 A | 11/1999 | Morris |
| 5,984,932 A | 11/1999 | Yoon |
| 5,984,938 A | 11/1999 | Yoon |
| 5,984,939 A | 11/1999 | Yoon |
| 5,989,277 A | 11/1999 | LeMaire, III et al. |
| 5,993,466 A | 11/1999 | Yoon |
| 5,993,467 A | 11/1999 | Yoon |
| 5,997,565 A | 12/1999 | Inoue |
| 6,004,332 A | 12/1999 | Yoon et al. |
| 6,004,335 A | 12/1999 | Vaitekunas et al. |
| 6,010,516 A | 1/2000 | Hulka et al. |
| 6,017,358 A | 1/2000 | Yoon et al. |
| 6,021,693 A | 2/2000 | Feng-Sing |
| 6,024,741 A | 2/2000 | Williamson et al. |
| 6,024,743 A | 2/2000 | Edwards |
| 6,024,744 A | 2/2000 | Kese et al. |
| 6,027,522 A | 2/2000 | Palmer |
| 6,030,384 A | 2/2000 | Nezhat |
| 6,033,399 A | 3/2000 | Gines |
| 6,039,733 A | 3/2000 | Buysse et al. |
| 6,041,679 A | 3/2000 | Slater et al. |
| 6,050,996 A | 4/2000 | Schmaltz et al. |
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| 6,059,782 A | 5/2000 | Novak et al. |
| 6,066,139 A | 5/2000 | Ryan et al. |
| 6,074,386 A | 6/2000 | Goble et al. |
| 6,077,287 A | 6/2000 | Taylor et al. |
| 6,080,180 A | 6/2000 | Yoon et al. |
| RE36,795 E | 7/2000 | Rydell |
| 6,083,223 A | 7/2000 | Baker |
| 6,086,586 A | 7/2000 | Hooven |
| 6,086,601 A | 7/2000 | Yoon |
| 6,090,107 A | 7/2000 | Borgmeier et al. |
| 6,096,037 A | 8/2000 | Mulier et al. |
| 6,099,550 A | 8/2000 | Yoon |
| 6,102,909 A | 8/2000 | Chen et al. |
| 6,106,542 A | 8/2000 | Toybin et al. |
| 6,110,171 A | 8/2000 | Rydell |
| 6,113,596 A | 9/2000 | Hooven et al. |
| 6,113,598 A | 9/2000 | Baker |
| 6,117,158 A | 9/2000 | Measamer et al. |
| 6,122,549 A | 9/2000 | Sharkey et al. |
| 6,123,701 A | 9/2000 | Nezhat |
| 6,126,658 A | 10/2000 | Baker |
| 6,126,665 A | 10/2000 | Yoon |
| 6,139,563 A | 10/2000 | Cosgrove, III et al. |
| 6,143,005 A | 11/2000 | Yoon et al. |
| 6,152,923 A | 11/2000 | Ryan |
| 6,162,220 A | 12/2000 | Nezhat |
| 6,171,316 B1 | 1/2001 | Kovac et al. |
| 6,174,309 B1 * | 1/2001 | Wrublewski et al. ........... 606/45 |
| 6,178,628 B1 | 1/2001 | Clemens et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,190,400 B1 | 2/2001 | Vandemoer et al. |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,206,893 B1 | 3/2001 | Klein et al. |
| 6,214,028 B1 | 4/2001 | Yoon et al. |
| 6,217,602 B1 | 4/2001 | Redmon |
| 6,217,615 B1 | 4/2001 | Sioshansi et al. |
| 6,221,039 B1 | 4/2001 | Durgin et al. |
| 6,223,100 B1 | 4/2001 | Green |
| 6,224,593 B1 | 5/2001 | Ryan et al. |
| 6,224,614 B1 | 5/2001 | Yoon |
| 6,228,080 B1 | 5/2001 | Gines |
| 6,228,083 B1 | 5/2001 | Lands et al. |
| 6,248,124 B1 | 6/2001 | Pedros et al. |
| 6,248,944 B1 | 6/2001 | Ito |
| 6,261,307 B1 | 7/2001 | Yoon et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,298,550 B1 | 10/2001 | Kirwan |
| 6,302,424 B1 | 10/2001 | Gisinger et al. |
| 6,319,262 B1 | 11/2001 | Bates et al. |
| 6,319,451 B1 | 11/2001 | Brune |
| 6,322,561 B1 | 11/2001 | Eggers et al. |
| 6,322,580 B1 | 11/2001 | Kanner |
| 6,325,795 B1 | 12/2001 | Lindemann et al. |
| 6,334,860 B1 | 1/2002 | Dorn |
| 6,334,861 B1 | 1/2002 | Chandler et al. |
| 6,350,264 B1 | 2/2002 | Hooven |
| 6,352,536 B1 | 3/2002 | Buysse et al. |
| 6,358,249 B1 | 3/2002 | Chen et al. |
| 6,358,259 B1 | 3/2002 | Swain et al. |
| 6,358,268 B1 | 3/2002 | Hunt et al. |
| 6,364,879 B1 | 4/2002 | Chen et al. |
| D457,958 S | 5/2002 | Dycus et al. |
| D457,959 S | 5/2002 | Tetzlaff et al. |
| 6,387,094 B1 | 5/2002 | Eitenmuller |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| 6,419,675 B1 | 7/2002 | Gallo, Sr. |
| 6,425,896 B1 | 7/2002 | Baltschun et al. |
| 6,432,112 B2 | 8/2002 | Brock et al. |
| 6,440,144 B1 | 8/2002 | Bacher |
| 6,443,952 B1 | 9/2002 | Mulier et al. |
| 6,443,970 B1 | 9/2002 | Schulze et al. |

| | | |
|---|---|---|
| 6,451,018 B1 | 9/2002 | Lands et al. |
| 6,458,125 B1 | 10/2002 | Cosmescu |
| 6,458,128 B1 | 10/2002 | Schulze |
| 6,458,130 B1 | 10/2002 | Frazier et al. |
| 6,461,352 B2 | 10/2002 | Morgan et al. |
| 6,461,368 B2 | 10/2002 | Fogarty et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,485,489 B2 | 11/2002 | Teirstein et al. |
| 6,494,888 B1 | 12/2002 | Laufer et al. |
| 6,500,176 B1 | 12/2002 | Truckai et al. |
| 6,506,196 B1 | 1/2003 | Laufer |
| 6,508,815 B1 | 1/2003 | Strul et al. |
| 6,511,480 B1 | 1/2003 | Tetzlaff et al. |
| 6,514,215 B1 | 2/2003 | Ouchi |
| 6,514,252 B2 | 2/2003 | Nezhat et al. |
| 6,517,539 B1 | 2/2003 | Smith et al. |
| 6,527,771 B1 | 3/2003 | Weadock et al. |
| 6,533,784 B2 | 3/2003 | Truckai et al. |
| 6,545,239 B2 | 4/2003 | Pedersen et al. |
| 6,558,385 B1 | 5/2003 | McClurken et al. |
| 6,562,037 B2 | 5/2003 | Paton et al. |
| 6,569,105 B1 | 5/2003 | Kortenbach et al. |
| 6,582,450 B2 | 6/2003 | Ouchi |
| 6,585,735 B1 | 7/2003 | Lands et al. |
| 6,602,252 B2 | 8/2003 | Mollenauer |
| 6,605,790 B2 | 8/2003 | Yoshida |
| 6,616,658 B2 | 9/2003 | Ineson |
| 6,616,661 B2 | 9/2003 | Wellman et al. |
| 6,620,161 B2 * | 9/2003 | Schulze et al. .................. 606/51 |
| 6,620,184 B2 | 9/2003 | De Laforcade et al. |
| 6,626,901 B1 | 9/2003 | Treat et al. |
| 6,638,287 B2 | 10/2003 | Danitz et al. |
| 6,641,595 B1 | 11/2003 | Moran et al. |
| 6,652,514 B2 | 11/2003 | Ellman et al. |
| 6,652,521 B2 | 11/2003 | Schulze |
| 6,656,175 B2 | 12/2003 | Francischelli et al. |
| 6,656,177 B2 | 12/2003 | Truckai et al. |
| 6,660,072 B2 | 12/2003 | Chatterjee |
| 6,663,639 B1 | 12/2003 | Laufer et al. |
| 6,663,641 B1 | 12/2003 | Kovac et al. |
| 6,666,854 B1 | 12/2003 | Lange |
| 6,669,696 B2 | 12/2003 | Bacher et al. |
| 6,673,092 B1 | 1/2004 | Bacher |
| 6,676,660 B2 | 1/2004 | Wampler et al. |
| 6,676,676 B2 | 1/2004 | Danitz et al. |
| 6,679,882 B1 | 1/2004 | Kornerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,693,246 B1 | 2/2004 | Rudolph et al. |
| 6,695,840 B2 | 2/2004 | Schulze |
| 6,702,810 B2 | 3/2004 | McClurken et al. |
| 6,723,092 B2 | 4/2004 | Brown et al. |
| 6,726,068 B2 | 4/2004 | Miller |
| 6,726,686 B2 | 4/2004 | Buysse et al. |
| 6,726,694 B2 | 4/2004 | Blatter et al. |
| 6,733,498 B2 | 5/2004 | Paton et al. |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,743,239 B1 | 6/2004 | Kuehn et al. |
| 6,743,240 B2 | 6/2004 | Smith et al. |
| 6,755,843 B2 | 6/2004 | Chung et al. |
| 6,756,553 B1 | 6/2004 | Yamaguchi et al. |
| 6,757,977 B2 | 7/2004 | Dambal et al. |
| D493,888 S | 8/2004 | Reschke |
| 6,770,072 B1 | 8/2004 | Truckai et al. |
| 6,773,409 B2 | 8/2004 | Truckai et al. |
| 6,773,432 B1 | 8/2004 | Clayman et al. |
| 6,773,434 B2 | 8/2004 | Ciarrocca |
| 6,773,441 B1 | 8/2004 | Laufer et al. |
| 6,775,575 B2 | 8/2004 | Bommannan et al. |
| 6,776,780 B2 | 8/2004 | Mulier et al. |
| 6,786,905 B2 | 9/2004 | Swanson et al. |
| 6,790,217 B2 | 9/2004 | Schulze et al. |
| 6,796,981 B2 | 9/2004 | Wham et al. |
| D496,997 S | 10/2004 | Dycus et al. |
| 6,800,825 B1 | 10/2004 | Sasaki et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,821,285 B2 | 11/2004 | Laufer et al. |
| 6,835,200 B2 | 12/2004 | Laufer et al. |
| 6,857,357 B2 | 2/2005 | Fujii |
| 6,860,880 B2 | 3/2005 | Treat et al. |
| 6,887,240 B1 | 5/2005 | Lands et al. |
| 6,889,116 B2 | 5/2005 | Jinno |
| 6,914,201 B2 | 7/2005 | Van Vooren et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| D509,297 S | 9/2005 | Wells |
| 6,942,662 B2 | 9/2005 | Goble et al. |
| 6,943,311 B2 | 9/2005 | Miyako |
| 6,953,430 B2 | 10/2005 | Kidooka |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,972,017 B2 | 12/2005 | Smith et al. |
| 6,977,495 B2 | 12/2005 | Donofrio |
| 6,979,786 B2 | 12/2005 | Aukland et al. |
| 6,981,628 B2 | 1/2006 | Wales |
| 6,987,244 B2 | 1/2006 | Bauer |
| 6,994,707 B2 | 2/2006 | Ellman et al. |
| 6,994,709 B2 | 2/2006 | Iida |
| 6,997,931 B2 | 2/2006 | Sauer et al. |
| 7,001,381 B2 | 2/2006 | Harano et al. |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 * | 5/2006 | Truckai et al. .................. 606/51 |
| 7,044,948 B2 | 5/2006 | Keppel |
| 7,052,489 B2 | 5/2006 | Griego et al. |
| 7,052,496 B2 | 5/2006 | Yamauchi |
| 7,063,715 B2 | 6/2006 | Onuki et al. |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,083,620 B2 | 8/2006 | Jahns et al. |
| 7,087,051 B2 | 8/2006 | Bourne et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,107,124 B2 | 9/2006 | Green |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| D533,942 S | 12/2006 | Kerr et al. |
| 7,145,757 B2 | 12/2006 | Shea et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| 7,153,314 B2 | 12/2006 | Laufer et al. |
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |

| | | |
|---|---|---|
| 7,160,299 B2 | 1/2007 | Baily |
| 7,169,146 B2 | 1/2007 | Truckai et al. |
| 7,179,255 B2 | 2/2007 | Lettice et al. |
| 7,179,258 B2 | 2/2007 | Buysse et al. |
| 7,195,631 B2 | 3/2007 | Dumbauld |
| D541,418 S | 4/2007 | Schechter et al. |
| 7,207,990 B2 | 4/2007 | Lands et al. |
| D541,938 S | 5/2007 | Kerr et al |
| 7,223,264 B2 | 5/2007 | Daniel et al. |
| 7,223,265 B2 | 5/2007 | Keppel |
| 7,232,440 B2 | 6/2007 | Dumbauld et al. |
| 7,241,288 B2 | 7/2007 | Braun |
| 7,241,296 B2 | 7/2007 | Buysse et al. |
| 7,244,257 B2 | 7/2007 | Podjahsky et al. |
| 7,246,734 B2 | 7/2007 | Shelto, IV |
| 7,248,944 B2 | 7/2007 | Green |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,300,435 B2 | 11/2007 | Wham et al. |
| 7,303,557 B2 | 12/2007 | Wham et al. |
| 7,311,709 B2 | 12/2007 | Truckai et al. |
| 7,314,471 B2 | 1/2008 | Holman |
| 7,318,823 B2 | 1/2008 | Sharps et al. |
| 7,329,256 B2 | 2/2008 | Johnson et al. |
| 7,329,257 B2 | 2/2008 | Kanehira et al. |
| D564,662 S | 3/2008 | Moses et al. |
| 7,338,526 B2 | 3/2008 | Steinberg |
| 7,342,754 B2 | 3/2008 | Fitzgerald et al. |
| 7,344,268 B2 | 3/2008 | Jigamian |
| D567,943 S | 4/2008 | Moses et al. |
| 7,367,976 B2 | 5/2008 | Lawes et al. |
| 7,377,920 B2 | 5/2008 | Buysse et al. |
| 7,384,420 B2 | 6/2008 | Dycus et al. |
| 7,384,421 B2 | 6/2008 | Hushka |
| 7,396,336 B2 | 7/2008 | Orszulak et al. |
| D575,395 S | 8/2008 | Hushka |
| D575,401 S | 8/2008 | Hixson et al. |
| 7,435,249 B2 | 10/2008 | Buysse et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| 7,458,972 B2 | 12/2008 | Keppel |
| 7,473,253 B2 | 1/2009 | Dycus et al. |
| 7,481,810 B2 | 1/2009 | Dumbauld et al. |
| 7,487,780 B2 | 2/2009 | Hooven |
| 7,491,201 B2 | 2/2009 | Shields et al. |
| 7,491,202 B2 | 2/2009 | Odom et al. |
| 7,500,975 B2 | 3/2009 | Cunningham et al. |
| 7,510,556 B2 | 3/2009 | Nguyen et al. |
| 7,513,898 B2 | 4/2009 | Johnson et al. |
| 7,540,872 B2 | 6/2009 | Schechter et al. |
| 7,549,995 B2 | 6/2009 | Schultz |
| 7,553,312 B2 | 6/2009 | Tetzlaff et al. |
| 2002/0013583 A1 | 1/2002 | Camran et al. |
| 2002/0049442 A1 | 4/2002 | Roberts et al. |
| 2002/0099372 A1 | 7/2002 | Schulze et al. |
| 2002/0107517 A1 | 8/2002 | Witt et al. |
| 2002/0111624 A1 | 8/2002 | Witt et al. |
| 2002/0188294 A1 | 12/2002 | Couture et al. |
| 2003/0014052 A1 | 1/2003 | Buysse et al. |
| 2003/0014053 A1 | 1/2003 | Nguyen et al. |
| 2003/0018331 A1* | 1/2003 | Dycus et al. ............... 606/48 |
| 2003/0018332 A1 | 1/2003 | Schmaltz et al. |
| 2003/0032956 A1 | 2/2003 | Lands et al. |
| 2003/0069570 A1 | 4/2003 | Witzel et al. |
| 2003/0069571 A1 | 4/2003 | Treat et al. |
| 2003/0078578 A1 | 4/2003 | Truckai et al. |
| 2003/0109875 A1 | 6/2003 | Tetzlaff et al. |
| 2003/0114851 A1 | 6/2003 | Truckai et al. |
| 2003/0139741 A1 | 7/2003 | Goble et al. |
| 2003/0139742 A1 | 7/2003 | Wampler et al. |
| 2003/0158548 A1 | 8/2003 | Phan et al. |
| 2003/0158549 A1 | 8/2003 | Swanson |
| 2003/0171747 A1 | 9/2003 | Kanehira et al. |
| 2003/0181910 A1 | 9/2003 | Dycus et al. |
| 2003/0199869 A1 | 10/2003 | Johnson et al. |
| 2003/0216732 A1 | 11/2003 | Truckai et al. |
| 2003/0220637 A1 | 11/2003 | Truckai et al. |
| 2003/0229344 A1 | 12/2003 | Dycus et al. |
| 2003/0236325 A1 | 12/2003 | Bonora |
| 2003/0236518 A1 | 12/2003 | Marchitto et al. |
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0064151 A1 | 4/2004 | Mollenauer |
| 2004/0073238 A1 | 4/2004 | Makower |
| 2004/0073256 A1 | 4/2004 | Marchitto et al. |
| 2004/0078035 A1 | 4/2004 | Kanehira et al. |
| 2004/0082952 A1 | 4/2004 | Dycus et al. |
| 2004/0087943 A1 | 5/2004 | Dycus et al. |
| 2004/0115296 A1 | 6/2004 | Duffin |
| 2004/0116924 A1 | 6/2004 | Dycus et al. |
| 2004/0116979 A1 | 6/2004 | Truckai et al. |
| 2004/0122423 A1 | 6/2004 | Dycus et al. |
| 2004/0143263 A1 | 7/2004 | Schechter et al. |
| 2004/0147925 A1 | 7/2004 | Buysse et al. |
| 2004/0148035 A1 | 7/2004 | Barrett et al. |
| 2004/0162557 A1 | 8/2004 | Tetzlaff et al. |
| 2004/0176762 A1 | 9/2004 | Lawes et al. |
| 2004/0193153 A1 | 9/2004 | Sarter et al. |
| 2004/0199181 A1* | 10/2004 | Knodel et al. ............... 606/139 |
| 2004/0210282 A1 | 10/2004 | Flock et al. |
| 2004/0224590 A1 | 11/2004 | Rawa et al. |
| 2004/0225288 A1 | 11/2004 | Buysse et al. |
| 2004/0230189 A1 | 11/2004 | Keppel |
| 2004/0236326 A1 | 11/2004 | Schulze et al. |
| 2004/0243125 A1 | 12/2004 | Dycus et al. |
| 2004/0249371 A1 | 12/2004 | Dycus et al. |
| 2004/0249374 A1 | 12/2004 | Tetzlaff et al. |
| 2004/0250419 A1 | 12/2004 | Sremcich et al. |
| 2004/0254573 A1 | 12/2004 | Dycus et al. |
| 2004/0260281 A1 | 12/2004 | Baxter, III et al. |
| 2005/0004564 A1 | 1/2005 | Wham et al. |
| 2005/0004568 A1 | 1/2005 | Lawes et al. |
| 2005/0004569 A1 | 1/2005 | Witt et al. |
| 2005/0004570 A1 | 1/2005 | Chapman et al. |
| 2005/0021025 A1 | 1/2005 | Buysse et al. |
| 2005/0021026 A1 | 1/2005 | Baily |
| 2005/0021027 A1 | 1/2005 | Shields et al. |
| 2005/0033278 A1 | 2/2005 | McClurken et al. |
| 2005/0059934 A1 | 3/2005 | Wenchell et al. |
| 2005/0096645 A1 | 5/2005 | Wellman et al. |
| 2005/0101951 A1 | 5/2005 | Wham et al. |
| 2005/0101952 A1 | 5/2005 | Lands et al. |
| 2005/0107784 A1 | 5/2005 | Moses et al. |
| 2005/0107785 A1 | 5/2005 | Dycus et al. |
| 2005/0113818 A1 | 5/2005 | Sartor et al. |
| 2005/0113819 A1 | 5/2005 | Wham et al. |
| 2005/0113826 A1 | 5/2005 | Johnson et al. |
| 2005/0113827 A1 | 5/2005 | Dumbauld et al. |
| 2005/0113828 A1 | 5/2005 | Shields et al. |
| 2005/0119655 A1 | 6/2005 | Moses et al. |
| 2005/0149017 A1 | 7/2005 | Dycus |
| 2005/0149151 A1 | 7/2005 | Orszulak et al. |
| 2005/0154387 A1 | 7/2005 | Moses et al. |
| 2005/0187547 A1 | 8/2005 | Sugi |
| 2005/0197659 A1 | 9/2005 | Bahney |
| 2005/0203504 A1 | 9/2005 | Wham et al. |
| 2005/0240179 A1 | 10/2005 | Buysse et al. |
| 2006/0052778 A1 | 3/2006 | Chapman et al. |
| 2006/0052779 A1 | 3/2006 | Hammill |
| 2006/0064085 A1 | 3/2006 | Schechter et al. |
| 2006/0064086 A1 | 3/2006 | Odom |
| 2006/0074417 A1 | 4/2006 | Cunningham et al. |
| 2006/0079888 A1 | 4/2006 | Mulier et al. |
| 2006/0079890 A1 | 4/2006 | Guerra |
| 2006/0079891 A1 | 4/2006 | Arts et al. |
| 2006/0079933 A1 | 4/2006 | Hushka et al. |
| 2006/0084973 A1 | 4/2006 | Hushka |
| 2006/0089670 A1 | 4/2006 | Hushka |
| 2006/0116675 A1 | 6/2006 | McClurken et al. |
| 2006/0129146 A1 | 6/2006 | Dycus et al. |
| 2006/0161150 A1 | 7/2006 | Keppel |
| 2006/0167450 A1 | 7/2006 | Johnson et al. |

| | | |
|---|---|---|
| 2006/0167452 A1 | 7/2006 | Moses et al. |
| 2006/0173452 A1 | 8/2006 | Buysse et al. |
| 2006/0189980 A1 | 8/2006 | Johnson et al. |
| 2006/0189981 A1 | 8/2006 | Dycus et al. |
| 2006/0190035 A1 | 8/2006 | Hushka et al. |
| 2006/0217709 A1 | 9/2006 | Couture et al. |
| 2006/0224158 A1 | 10/2006 | Odom et al. |
| 2006/0229666 A1 | 10/2006 | Suzuki et al. |
| 2006/0253126 A1 | 11/2006 | Bjerken et al. |
| 2006/0259036 A1 | 11/2006 | Tetzlaff et al. |
| 2006/0264922 A1 | 11/2006 | Sartor et al. |
| 2006/0264931 A1 | 11/2006 | Chapman et al. |
| 2006/0271038 A1 | 11/2006 | Johnson et al. |
| 2006/0283093 A1 | 12/2006 | Petrovic et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0043352 A1 | 2/2007 | Garrison et al. |
| 2007/0043353 A1 | 2/2007 | Dycus et al. |
| 2007/0055231 A1 | 3/2007 | Dycus et al. |
| 2007/0060919 A1 | 3/2007 | Isaacson et al. |
| 2007/0062017 A1 | 3/2007 | Dycus et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1 | 5/2007 | Dumbauld et al. |
| 2007/0118111 A1 | 5/2007 | Weinberg |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |
| 2007/0156140 A1 | 7/2007 | Baily |
| 2007/0173811 A1 | 7/2007 | Couture et al. |
| 2007/0173814 A1 | 7/2007 | Hixson et al. |
| 2007/0179499 A1 | 8/2007 | Garrison |
| 2007/0198011 A1 | 8/2007 | Sugita |
| 2007/0203485 A1 | 8/2007 | Keppel |
| 2007/0213706 A1 | 9/2007 | Dumbauld et al. |
| 2007/0213707 A1 | 9/2007 | Dumbauld et al. |
| 2007/0213708 A1 | 9/2007 | Dumbauld et al. |
| 2007/0213712 A1 | 9/2007 | Buysse et al. |
| 2007/0255279 A1 | 11/2007 | Buysse et al. |
| 2007/0260235 A1 | 11/2007 | Podhajsky |
| 2007/0260238 A1 | 11/2007 | Guerra |
| 2007/0260241 A1 | 11/2007 | Dalla Betta et al. |
| 2007/0260242 A1 | 11/2007 | Dycus et al. |
| 2007/0265616 A1 | 11/2007 | Couture et al. |
| 2008/0004616 A1 | 1/2008 | Patrick |
| 2008/0009860 A1 | 1/2008 | Odom |
| 2008/0015575 A1 | 1/2008 | Odom et al. |
| 2008/0021450 A1 | 1/2008 | Couture |
| 2008/0033428 A1 | 2/2008 | Artale et al. |
| 2008/0039835 A1 | 2/2008 | Johnson et al. |
| 2008/0039836 A1 | 2/2008 | Odom et al. |
| 2008/0045947 A1 | 2/2008 | Johnson et al. |
| 2008/0058802 A1 | 3/2008 | Couture et al. |
| 2008/0082100 A1 | 4/2008 | Orton et al. |
| 2008/0091189 A1 | 4/2008 | Carlton |
| 2008/0114356 A1 | 5/2008 | Johnson et al. |
| 2008/0167651 A1 | 7/2008 | Tetzlaff et al. |
| 2008/0195093 A1 | 8/2008 | Couture et al. |
| 2008/0215051 A1 | 9/2008 | Buysse et al. |
| 2008/0243120 A1 | 10/2008 | Lawes et al. |
| 2008/0249527 A1 | 10/2008 | Couture |
| 2008/0312653 A1 | 12/2008 | Arts et al. |
| 2008/0319442 A1 | 12/2008 | Unger et al. |
| 2009/0012520 A1 | 1/2009 | Hixson et al. |
| 2009/0018535 A1 | 1/2009 | Schechter et al. |
| 2009/0024126 A1 | 1/2009 | Artale et al. |
| 2009/0043304 A1 | 2/2009 | Tetzlaff et al. |
| 2009/0048596 A1 | 2/2009 | Shields et al. |
| 2009/0062794 A1 | 3/2009 | Buysse et al. |
| 2009/0082766 A1 | 3/2009 | Unger et al. |
| 2009/0082767 A1 | 3/2009 | Unger et al. |
| 2009/0082769 A1 | 3/2009 | Unger et al. |
| 2009/0088738 A1 | 4/2009 | Guerra et al. |
| 2009/0088739 A1 | 4/2009 | Hushka et al. |
| 2009/0088740 A1 | 4/2009 | Guerra et al. |
| 2009/0088741 A1 | 4/2009 | Hushka et al. |
| 2009/0088744 A1 | 4/2009 | Townsend |
| 2009/0088745 A1 | 4/2009 | Hushka et al. |
| 2009/0088746 A1 | 4/2009 | Hushka et al. |
| 2009/0088747 A1 | 4/2009 | Hushka et al. |
| 2009/0088748 A1 | 4/2009 | Guerra et al. |
| 2009/0088749 A1 | 4/2009 | Hushka et al. |
| 2009/0088750 A1 | 4/2009 | Hushka et al. |
| 2009/0112206 A1 | 4/2009 | Dumbauld et al. |
| 2009/0131934 A1 | 5/2009 | Odom et al. |
| 2009/0149853 A1 | 6/2009 | Shields et al. |
| 2009/0149854 A1 | 6/2009 | Cunningham et al. |
| 2009/0171350 A1 | 7/2009 | Dycus et al. |
| 2009/0171353 A1 | 7/2009 | Johnson et al. |
| 2009/0182327 A1 | 7/2009 | Unger |
| 2009/0187188 A1 | 7/2009 | Guerra et al. |

FOREIGN PATENT DOCUMENTS

| | | |
|---|---|---|
| DE | 2415263 | 10/1975 |
| DE | 2514501 | 10/1976 |
| DE | 2627679 | 1/1977 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 29616210 | 1/1997 |
| DE | 19608716 | 4/1997 |
| DE | 19751108 | 5/1999 |
| DE | 19738457 | 1/2009 |
| EP | 0364216 A1 | 4/1990 |
| EP | 0467501 | 1/1992 |
| EP | 518230 A1 | 12/1992 |
| EP | 541 930 B1 | 5/1993 |
| EP | 0572131 | 12/1993 |
| EP | 584787 A1 | 3/1994 |
| EP | 0589453 A2 | 3/1994 |
| EP | 0589555 | 3/1994 |
| EP | 0623316 A1 | 11/1994 |
| EP | 0624348 A2 | 11/1994 |
| EP | 0650701 A1 | 5/1995 |
| EP | 0694290 A3 | 3/1996 |
| EP | 0717966 A1 | 6/1996 |
| EP | 0754437 A3 | 3/1997 |
| EP | 0517243 | 9/1997 |
| EP | 853922 A1 | 7/1998 |
| EP | 0875209 A1 | 11/1998 |
| EP | 0878169 A1 | 11/1998 |
| EP | 0887046 A3 | 1/1999 |
| EP | 0923907 A1 | 6/1999 |
| EP | 0986990 A1 | 3/2000 |
| EP | 1034747 A1 | 9/2000 |
| EP | 1034748 A1 | 9/2000 |
| EP | 1025807 A3 | 10/2000 |
| EP | 1034746 A3 | 10/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1082944 A1 | 3/2001 |
| EP | 1159926 A2 | 12/2001 |
| EP | 1177771 | 2/2002 |
| EP | 1301135 A | 4/2003 |
| EP | 1330991 A1 | 7/2003 |
| EP | 1486177 A2 | 6/2004 |
| EP | 1472984 A1 | 11/2004 |
| EP | 0774232 | 1/2005 |
| EP | 1527747 A2 | 5/2005 |
| EP | 1530952 A1 | 5/2005 |
| EP | 1532932 A1 | 5/2005 |
| EP | 1535581 A2 | 6/2005 |
| EP | 1609430 A1 | 12/2005 |
| EP | 1632192 A1 | 3/2006 |
| EP | 1642543 | 4/2006 |
| EP | 1645238 A1 | 4/2006 |

| | | |
|---|---|---|
| EP | 1645240 A2 | 4/2006 |
| EP | 1649821 | 4/2006 |
| EP | 1707143 A1 | 10/2006 |
| EP | 1769765 | 4/2007 |
| EP | 1769766 | 4/2007 |
| EP | 1929970 | 6/2008 |
| EP | 1683496 | 12/2008 |
| GB | 623316 | 5/1949 |
| GB | 1490585 | 11/1977 |
| GB | 2214430 A | 6/1989 |
| GB | 2213416 | 8/1989 |
| JP | 501068 | 9/1984 |
| JP | 502328 | 3/1992 |
| JP | 5-5106 | 1/1993 |
| JP | 5-40112 | 2/1993 |
| JP | 06343644 A2 | 12/1994 |
| JP | 07265328 A2 | 10/1995 |
| JP | 08056955 A2 | 3/1996 |
| JP | 08252263 A2 | 10/1996 |
| JP | 09010223 A2 | 1/1997 |
| JP | 11244298 A2 | 9/1999 |
| JP | 2000342599 A2 | 12/2000 |
| JP | 2000350732 A2 | 12/2000 |
| JP | 2001008944 A2 | 1/2001 |
| JP | 2001029356 A2 | 2/2001 |
| JP | 2001128990 A2 | 5/2001 |
| SU | 401367 | 11/1974 |
| WO | WO89/00757 | 1/1989 |
| WO | WO 92/04873 | 4/1992 |
| WO | WO 92/06642 | 4/1992 |
| WO | WO 93/21845 | 11/1993 |
| WO | WO 94/08524 A | 4/1994 |
| WO | WO94/20025 | 9/1994 |
| WO | WO 95/02369 | 1/1995 |
| WO | WO 95/07662 | 3/1995 |
| WO | WO95/15124 | 6/1995 |
| WO | WO96/05776 | 2/1996 |
| WO | WO 96/22056 | 7/1996 |
| WO | WO 96/13218 | 9/1996 |
| WO | WO 97/00646 | 1/1997 |
| WO | WO 97/00647 | 1/1997 |
| WO | WO 97/10764 | 3/1997 |
| WO | WO 97/24073 | 7/1997 |
| WO | WO 97/24993 | 7/1997 |
| WO | WO 98/27880 | 7/1998 |
| WO | WO 99/03407 | 1/1999 |
| WO | WO 99/03408 | 1/1999 |
| WO | WO 99/03409 | 1/1999 |
| WO | WO 99/12488 | 3/1999 |
| WO | WO 99/23933 | 5/1999 |
| WO | WO 99/40857 | 8/1999 |
| WO | WO 99/40861 | 8/1999 |
| WO | WO 99/51158 | 10/1999 |
| WO | WO 99/66850 A | 12/1999 |
| WO | WO 00/24330 | 5/2000 |
| WO | WO 00/24331 | 5/2000 |
| WO | WO 00/36986 | 6/2000 |
| WO | WO 00/41638 | 7/2000 |
| WO | WO00/47124 | 8/2000 |
| WO | WO 00/53112 | 9/2000 |
| WO | WO 01/17448 A | 3/2001 |
| WO | WO 01/54604 | 8/2001 |
| WO | WO 02/07627 | 1/2002 |
| WO | WO 02/067798 A1 | 9/2002 |
| WO | WO 02/080783 | 10/2002 |
| WO | WO 02/080784 | 10/2002 |
| WO | WO 02/080785 | 10/2002 |
| WO | WO 02/080786 | 10/2002 |
| WO | WO 02/080793 | 10/2002 |
| WO | WO 02/080794 | 10/2002 |
| WO | WO 02/080795 | 10/2002 |
| WO | WO 02/080796 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | WO 03/061500 | 7/2003 |
| WO | WO 03/090630 A3 | 11/2003 |
| WO | WO 03/101311 | 12/2003 |
| WO | WO 2004/032776 A1 | 4/2004 |
| WO | WO 2004/032777 | 4/2004 |
| WO | WO 2004/052221 | 6/2004 |
| WO | WO 2004/073488 A2 | 9/2004 |
| WO | WO 2004/073490 | 9/2004 |
| WO | WO2004/073753 | 9/2004 |
| WO | WO 2004/082495 | 9/2004 |
| WO | WO 2004/098383 | 11/2004 |
| WO | WO 2004/103156 | 12/2004 |
| WO | 2005/004734 A1 | 1/2005 |
| WO | WO2005/004735 | 1/2005 |
| WO | WO 2005/110264 | 11/2005 |
| WO | WO 2008/045348 | 4/2008 |
| WO | WO 2008/045350 | 4/2008 |

OTHER PUBLICATIONS

Int'l Search Report EP 06 024122.1 dated Mar. 19, 2007.
Int'l Search Report EP 07 001480.8 dated Apr. 12, 2007.
Int'l Search Report EP 07 001488.1 dated May 29, 2007.
Int'l Search Report—Extended EP 07 009029.5 dated Jul. 12, 2007.
Int'l Search Report EP 07 009321.6 dated Aug. 17, 2007.
Int'l Search Report EP 05016399 dated Jan. 5, 2006.
Int'l Search Report EP 06005185.1 dated Apr. 18, 2006.
Int'l Search Report EP 06008779.8 dated Jun. 13, 2006.
Int'l Search Report EP 1683496 dated Jun. 13, 2006.
Int'l Search Report EP 06006716 dated Aug. 4, 2006.
Int'l Search Report EP 06014461.5 dated Oct. 20, 2006.
Int'l Search Report EP 06020584.6 dated Jan. 12, 2007.
Int'l Search Report EP 06020583.8 dated Jan. 30, 2007.
Int'l Search Report EP 06020756.0 dated Feb. 5, 2007.
Int'l Search Report EP 06024123.9 dated Feb. 26, 2007.
Sigel et al. "The Mechanism of Blood Vessel Closure by High Frequency Electrocoagulation" Surgery Gynecology & Obstetrics, Oct. 1965, pp. 823-831.
Bergdahl et al. "Studies on Coagulation and the Development of an Automatic Computerized Bipolar Coagulator" J.Neurosurg, vol. 75, Jul. 1991, pp. 148-151.
Kennedy et al. "High-burst-strength, feedback-controlled bipolar vessel sealing" Surgical Endoscopy (1998) 12: 876-878.
Peterson et al. "Comparison of Healing Process Following Ligation with Sutures and Bipolar Vessel Sealing" Surgical Technology International (2001).
Linehan et al. "A Phase I Study of the LigaSure Vessel Sealing System in Hepatic Surgery" Section of HPB Surger, Washington University School of Medicine, St. Louis MO, Presented at AHPBA, Feb. 2001.
Johnson et al. "Evaluation of the LigaSure Vessel Sealing System in Hemorrhoidectormy" American College of Surgeons (ACS) Clinicla Congress Poster (2000).
Sayfan et al. "Sutureless Closed Hemorrhoidectomy: A New Technique" Annals of Surgery vol. 234 No. 1 Jul. 2001 pp. 21-24.
Heniford et al. "Initial Results with an Electrothermal Bipolar Vessel Sealer" Surgical Endoscopy (2000) 15:799-801.
Heniford et al. "Initial Research and Clinical Results with an Electrothermal Bipolar Vessel Sealer" Oct. 1999.
McLellan et al. "Vessel Sealing for Hemostasis During Pelvic Surgery" Int'l Federation of Gynecology and Obstetrics FIGO World Congress 2000, Washington, D.C.
Levy et al. "Use of a New Energy-based Vessel Ligation Device During Vaginal Hysterectomy" Int'l Federation of Gynecology and Obstetrics (FIGO) World Congress 1999.
Crawford et al. "Use of the LigaSure Vessel Sealing System in Urologic Cancer Surger" Grand Rounds in Urology 1999 vol. 1 Issue 4 pp. 10-17.
Rothenberg et al. "Use of the LigaSure Vessel Sealing System in Minimally Invasive Surgery in Children" Int'l Pediatric Endosurgery Group (IPEG) 2000.
Palazzo et al. "Randomized clinical trial of Ligasure versus open haemorrhoidectomy" British Journal of Surgery 2002, 89, 154-157.
"Innovations in Electrosurgery" Sales/Product Literature; Dec. 31, 2000.

LigaSure Vessel Sealing System, the Seal of Confidence in General, Gynecologic, Urologic, and Laparaoscopic Surgery Sales/Product Literature; Jan. 2004.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC 2003.
"Reducing Needlestick Injuries in the Operating Room" Sales/Product Literature 2001.
Chung et al., "Clinical Experience of Sutureless Closed Hemorrhoidectomy with LigaSure" Diseases of the Colon & Rectum vol. 46, No. 1 Jan. 2003.
Strasberg et al., "Use of a Bipolar Vessel-Sealing Device for Parenchymal Transection During Liver Surgery" Journal of Gastrointestinal Surgery. vol. 6, No. 4, Jul./Aug. 2002, pp. 569-574.
Paul G. Horgan, "A Novel Technique for Parenchymal Division During Hepatectomy" The American Journal of Surgery, vol. 181, No. 3, Apr. 2001 pp. 236-237.
W. Scott Helton, "LigaSure Vessel Sealing System: Revolutionary Hemostasis Product for General Surgery" Sales/Product Literature 1999.
Michael Choti, "Abdominoperineal Resection with the LigaSure Vessel Sealing System and LigaSure Atlas 20 cm Open Instrument" Innovations That Work, Jun. 2003.
Craig Johnson, "Use of the LigaSure Vessel Sealing System in Bloodless Hemorrhoidectomy" Innovations That Work, Mar. 2000.
Muller et al., "Extended Left Hemicolectomy Using the LigaSure Vessel Sealing System" Innovations That Work, Sep. 1999.
Herman et al., "Laparoscopic Intestinal Resection Wth the LigaSure Vessel Sealing System: A Case Report" Innovations That Work, Feb. 2002.
Carus et al., "Initial Experience With The LigaSure Vessel Sealing System in Abdominal Surgery" Innovations That Work, Jun. 2002.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
Levy et al., "Update on Hysterectomy—New Technologies and Techniques" OBG Management, Feb. 2003.
Barbara Levy, "Use of a New Vessel Ligation Device During Vaginal Hysterectomy" FIGO 2000, Washington, D.C.
McLellan et al. "Vessel Sealing For Hemostasis During Gynecologic Surgery" Sales/Product Literature 1999.
Sengupta et al., "Use of a Computer-Controlled Bipolar Diathermy System in Radical Prostatectomies and Other Open Urological Surgery" ANZ Journal of Surgery (2001) 71.9 pp. 538-540.
Olsson et al. "Radical Cystectomy in Females" Current Surgical Techniques in Urology, vol. 14, Issue 3, 2001.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
E. David Crawford "Evaluation of a New Vessel Sealing Device in Urologic Cancer Surgery" Sales/Products Literature 2000.
Joseph Ortenberg "LigaSure System Used in Laparoscopic 1st and 2nd Stage Orchiopexy" Innovations That Work, Nov. 2002.
Koyle et al., "Laparoscopic Palomo Varicocele Ligation in Children and Adolescents" Pediatric Endosurgery & Innovative Techniques, vol. 6, No. 1, 2002.
Dulemba et al. "Use of a Bipolar Electrothermal Vessel Sealer in Laparoscopically Assisted Vaginal Hysterectomy" Sales/Product Literature; Jan. 2004.
Johnson et al. "Evaluation of a Bipolar electrothermal Vessel Sealing Device in Hemorrhoidectomy" Sales/Product Literature; Jan. 2004.
Int'l Search Report PCT/US98/18640 dated Dec. 17, 1998.
Int'l Search Report PCT/US98/23950 dated Dec. 29, 1998.
Int'l Search Report PCT/US99/24869 dated Feb. 3, 2000.
Int'l Search Report PCT/US01/11218 dated Aug. 3, 2001.
International Search Report PCT/US01/11224 dated Nov. 13, 2001.
Int'l Search Report PCT/US01/11340 dated Aug. 7, 2001.
Int'l Search Report PCT/US01/11420 dated Oct. 8, 2001.
Int'l Search Report PCT/US02/01890 dated Jul. 17, 2002.
Int'l Search Report PCT/US02/11100 dated Jul. 9, 2002.
Int'l Search Report PCT/US04/03436 dated Oct. 5, 2004.
Int'l Search Report PCT/US04/13273 dated Nov. 22, 2004.
Int'l Search Report PCT/US04/15311 dated Nov. 18, 2004.
Int'l Search Report EP 98944778 dated Oct. 31, 2000.
Int'l Search Report EP 98958575.7 dated Sep. 20, 2002.
Int'l Search Report EP 04027314 dated Mar. 10, 2005.
Int'l Search Report EP 04027479 dated Mar. 8, 2005.
Int'l Search Report EP 04027705 dated Feb. 3, 2005.
Int'l Search Report EP 04013772 dated Apr. 1, 2005.
Int'l Search Report EP 05013463.4 dated Sep. 28, 2005.
Int'l Search Report EP 05013895 dated Oct. 14, 2005.
Int'l Search Report EP 05017281 dated Nov. 16, 2005.
Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021779.3 dated Jan. 18, 2006.
Int'l Search Report EP 05021197.8 dated Jan. 31, 2006.
Int'l Search Report EP 05021937.7 dated Jan. 13, 2006.
Int'l Search Report—extended- EP 05021937.7 dated Mar. 6, 2006.
Int'l Search Report EP 05023017.6 dated Feb. 16, 2006.
Int'l Search Report EP 05021780.1 dated Feb. 9, 2006.
Int'l Search Report EP 06002279.5 dated Mar. 22, 2006.
Vallfors, et al., Automatically Controlled Bipolar Electrocoagulation—'COA-COMP', Neurosurg. Rev. (1984), pp. 187-190.
Int'l Search Report EP 06 020574.7 dated Sep. 21, 23007.
Int'l Search Report EP 07 010672.9 dated Oct. 1, 2007.
Int'l Search Report EP 07 013779.9 dated Oct. 18, 2007
Int'l Search Report EP 07 009026.1 dated Sep. 12, 2007
Int'l Search Report EP 07 015601.3 dated Dec. 6, 2007.
Int'l Search Report EP 07 015191.5 dated Dec. 19, 2007.
Int'l Search Report EP 07 020283.3 dated Jan. 16, 2008.
Sampayan et al, "Multilayer Ultra-High Gradient Insulator Technology" Discharges and Electrical Insulation in Vacuum, 1998. Netherlands Aug.17-21, 1998; vol. 2, pp. 740-743.
Crouch et al. "A Velocity-Dependent Model for Needle Insertion in Soft Tissue" MICCAI 2005; LNCS 3750 pp. 624-632, Dated: 2005.
Int'l Search Report EP 98957771 dated Aug. 9, 2001.
Int'l Search Report EP 05002671.5 dated Dec. 22, 2008.
Int'l Search Report EP 05002674.9 dated Jan. 16, 2009.
Int'l Search Report EP 05019429.9 dated May 6, 2008.
Int'l Search Report EP 06008515.6 dated Jan. 8, 2009.
Int'l Search Report EP 07 014016 dated Jan. 28, 2008.
Int'l Search Report EP 07 021646.0 dated Jul. 9, 2008.
Int'l Search Report EP 07 021647.8 dated May 2, 2008.
Int'l Search Report EP 08 02692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 Dated Jun. 15, 2009.
Int'l Search Report EP 09 152898.4 Dated Jun. 10, 2009.
Int'l Search Report PCT/US98/24281 dated Feb. 22, 1999.
Int'l Search Report PCT/US03/28534 dated Dec. 19, 2003.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.

* cited by examiner

MECHANISM FOR DIVIDING TISSUE IN A HEMOSTAT-STYLE INSTRUMENT

CROSS REFERENCE TO RELATED APPLICATION

This application claims the benefit of priority to U.S. Provisional Application Ser. No. 60/616,968 filed on Oct. 8, 2004 entitled "MECHANISM FOR DIVIDING TISSUE IN A HEMOSTAT-STYLE INSTRUMENT" the entire contents of which being incorporated by reference herein.

BACKGROUND

The present disclosure relates to forceps used for open surgical procedures. More particularly, the present disclosure relates to an open forceps which applies a combination of mechanical clamping pressure and electrosurgical energy to seal tissue and a cutting device which is selectively activatable to sever tissue.

TECHNICAL FIELD

A forceps is a plier-like instrument which relies on mechanical action between its jaws to grasp, clamp and constrict vessels or tissue therebetween. So-called "open forceps" are commonly used in open surgical procedures whereas "endoscopic forceps" or "laparoscopic forceps" are, as the name implies, used for less invasive endoscopic surgical procedures. Electrosurgical forceps (open or endoscopic) utilize both mechanical clamping action and electrical energy to effect hemostasis by heating tissue and blood vessels to coagulate and/or cauterize tissue.

Certain surgical procedures require more than simply cauterizing tissue and rely on the unique combination of clamping pressure, precisely controlling the application of electrosurgical energy and the gap distance (i.e., distance between opposing jaw members or opposing conducting surfaces when closed about tissue) to "seal" tissue, vessels and certain vascular bundles.

Vessel sealing or tissue sealing is a recently-developed technology which utilizes a unique combination of radiofrequency energy, pressure and gap control to effectively seal or fuse tissue between two opposing jaw members or sealing plates. Vessel or tissue sealing is more than "cauterization" which is defined as the use of heat to destroy tissue (also called "diathermy" or "electrodiathermy") and vessel sealing is more than "coagulation" which is defined as a process of desiccating tissue wherein the tissue cells are ruptured and dried. "Vessel sealing" is defined as the process of liquefying the collagen, elastin and ground substances in the tissue so that it reforms into a fused mass with significantly-reduced demarcation between the opposing tissue structures.

In order to effectively "seal" tissue or vessels, two predominant mechanical parameters must be accurately controlled: 1) the pressure applied to the vessel or tissue; and 2) the gap distance between the conductive tissue contacting surfaces (electrodes). As can be appreciated, both of these parameters are affected by the thickness of the tissue being sealed. Accurate application of pressure is important for several reasons: to reduce the tissue impedance to a low enough value that allows enough electrosurgical energy through the tissue; to overcome the forces of expansion during tissue heating; and to contribute to the end tissue thickness which is an indication of a good seal. It has been determined that a good seal for certain tissues is optimum between 0.001 inches and 0.006 inches.

With respect to smaller vessels or tissue, the pressure applied becomes less relevant and the gap distance between the electrically conductive surfaces becomes more significant for effective sealing. In other words, the chances of the two electrically conductive surfaces touching during activation increases as the tissue thickness and the vessels become smaller.

Commonly owned, U.S. Pat. No. 6,511,480, PCT Patent Application Nos. PCT/US01/11420 and PCT/US01/11218, U.S. patent application Ser. Nos. 10/116,824, 10/284,562 and 10/299,650 all describe various open surgical forceps which seal tissue and vessels. All of these references are hereby incorporated by reference herein. In addition, several journal articles have disclosed methods for sealing small blood vessels using electrosurgery. An article entitled Studies on Coagulation and the Development of an Automatic Computerized Bipolar Coagulator, J. Neurosurg., Volume 75, July 1991, describes a bipolar coagulator which is used to seal small blood vessels. The article states that it is not possible to safely coagulate arteries with a diameter larger than 2 to 2.5 mm. A second article is entitled Automatically Controlled Bipolar Electrocoagulation—"COA-COMP", Neurosurg. Rev. (1984), pp. 187-190, describes a method for terminating electrosurgical power to the vessel so that charring of the vessel walls can be avoided.

Typically and particularly with respect to open electrosurgical procedures, once a vessel is sealed, the surgeon has to remove the sealing instrument from the operative site, substitute a new instrument and accurately sever the vessel along the newly formed tissue seal. As can be appreciated, this additional step may be both time consuming (particularly when sealing a significant number of vessels) and may contribute to imprecise separation of the tissue along the sealing line due to the misalignment or misplacement of the severing instrument along the center of the tissue sealing line.

Many endoscopic vessel sealing instruments have been designed which incorporate a knife or blade member which effectively severs the tissue after forming a tissue seal. For example, commonly-owned U.S. application Ser. Nos. 10/116,944; 10/179,863; and 10/460,926 all describe endoscopic instruments which effectively seals and cuts tissue along the tissue seal. Other instruments include blade members or shearing members which simply cut tissue in a mechanical and/or electromechanical manner and are relatively ineffective for vessel sealing purposes.

There exists a need to develop an open electrosurgical forceps which is simple, reliable and inexpensive to manufacture and which effectively seals tissue and vessels and which allows a surgeon to utilize the same instrument to effectively sever the tissue along the newly formed tissue seal.

SUMMARY

Forceps for use in open surgical procedures are provided. According to one aspect of the present disclosure, an open electrosurgical forceps for sealing tissue is provided. The forceps includes first and second shaft portions pivotably associated with one another. Each shaft portion has a jaw member disposed at a distal end thereof. The jaw members are movable from a first position in spaced relation relative to one another to at least one subsequent position wherein the jaw members cooperate to grasp tissue therebetween. Each of the jaw members includes an electrically conductive sealing surface for communicating electrosurgical energy through tissue held therebetween. At least one of the jaw members includes a slot formed through the sealing surface thereof.

The forceps further includes a cutting mechanism operatively associated with the first and second jaw members. The cutting mechanism includes a cutting element disposed within the slot of the at least one jaw member. The cutting element is movable from a first position wherein the cutting element is retracted within the slot of the at least one jaw member and a second position in which the cutting element at least partially projects from the sealing surface of the at least one jaw member. The cutting mechanism further includes an actuator operatively associated with the cutting element which upon movement thereof selectively advances the cutting element from the first position to the second positions.

In one embodiment, the actuator is integrally associated with the cutting element. The cutting mechanism is pivotable about a pivot which connects the first and second jaw members. The actuator is spaced a distance from the first shaft portion. The actuator selectively activates the cutting element when moved relative to the first shaft portion.

In another embodiment, the cutting mechanism may include a drive rod extending through a channel formed in at least one of the first and second shaft portions. The drive rod includes a distal end operatively connected to the cutting element. The cutting mechanism may further include a tab operatively connected to the drive rod for manipulating the drive rod to urge the cutting element between the first and second positions.

The cutting element is supported in the slot of the jaw member such that proximal displacement of the drive rod urges the cutting element from within the slot of the jaw member to cut tissue. Desirably, the cutting element includes at least one angled slot defined therethrough which receives a pivot pin fixed to one of the jaw members.

In one embodiment, each angled slot formed in the cutting element includes a first portion in close proximity to the sealing surface and a second portion extending distally and away from the sealing surface. Proximal movement of the drive rod urges the cutting element from the first position to the second position by a camming action between the pin and the slot formed in the cutting element.

The open electrosurgical forceps may further include a biasing element for urging the drive rod to a distal-most position. The cutting element is pivotably disposed within the slot of the jaw member. The cutting element projects out through the jaw member and defines a camming surface.

In one embodiment, the second shaft portion reciprocably supports the actuator. The actuator is movable from a first position spaced from the cutting element to a second position in contact with the cutting element. In use, displacement of the actuator from the first position to the second position, the actuator engages the camming surface of the cutting element and urges the cutting element from the first position to the second position.

The open electrosurgical forceps may further include a biasing element for urging the cutting element to the first position. It is envisioned that movement of the actuator pivots the cutting element between the first and second positions.

According to another aspect of the present disclosure, the open electrosurgical forceps may include a pair of shaft portions pivotably coupled to one another at a pivot point. Each shaft portion includes a jaw member at a distal end thereof for grasping tissue therebetween. Each jaw member includes a sealing surface for conducting electrosurgical energy through tissue grasped therebetween and one of the sealing surfaces has a slot formed therein. The forceps further includes a cutting mechanism operatively coupled to the shaft portions and has a cutting element operatively secured proximate the distal end of the forceps. The cutting mechanism is selectively movable from a first position in which the cutting element is retracted within the slot and a second position in which the cutting element at least partially projects from the slot to cut tissue disposed between the jaw members.

In one embodiment, the cutting mechanism includes a drive rod extending through a channel formed in at least one of the first and second shaft portions. The drive rod includes a distal end operatively connected to the cutting element. The cutting mechanism further includes a tab operatively connected to the drive rod for manipulating the drive rod to urge the cutting element between the first and second positions.

The cutting element is operatively engaged in the slot of the one jaw member such that axial displacement of the drive rod results in transverse displacement of the cutting element from the slot to cut tissue disposed between jaw members.

DESCRIPTION OF THE DRAWINGS

Various embodiments of the present disclosure are described with reference to the following drawing figures. It should be understood, however, that the drawings are designed for the purpose of illustration only and not as a definition of the limits of the invention.

DETAILED DESCRIPTION

Figure 1A:
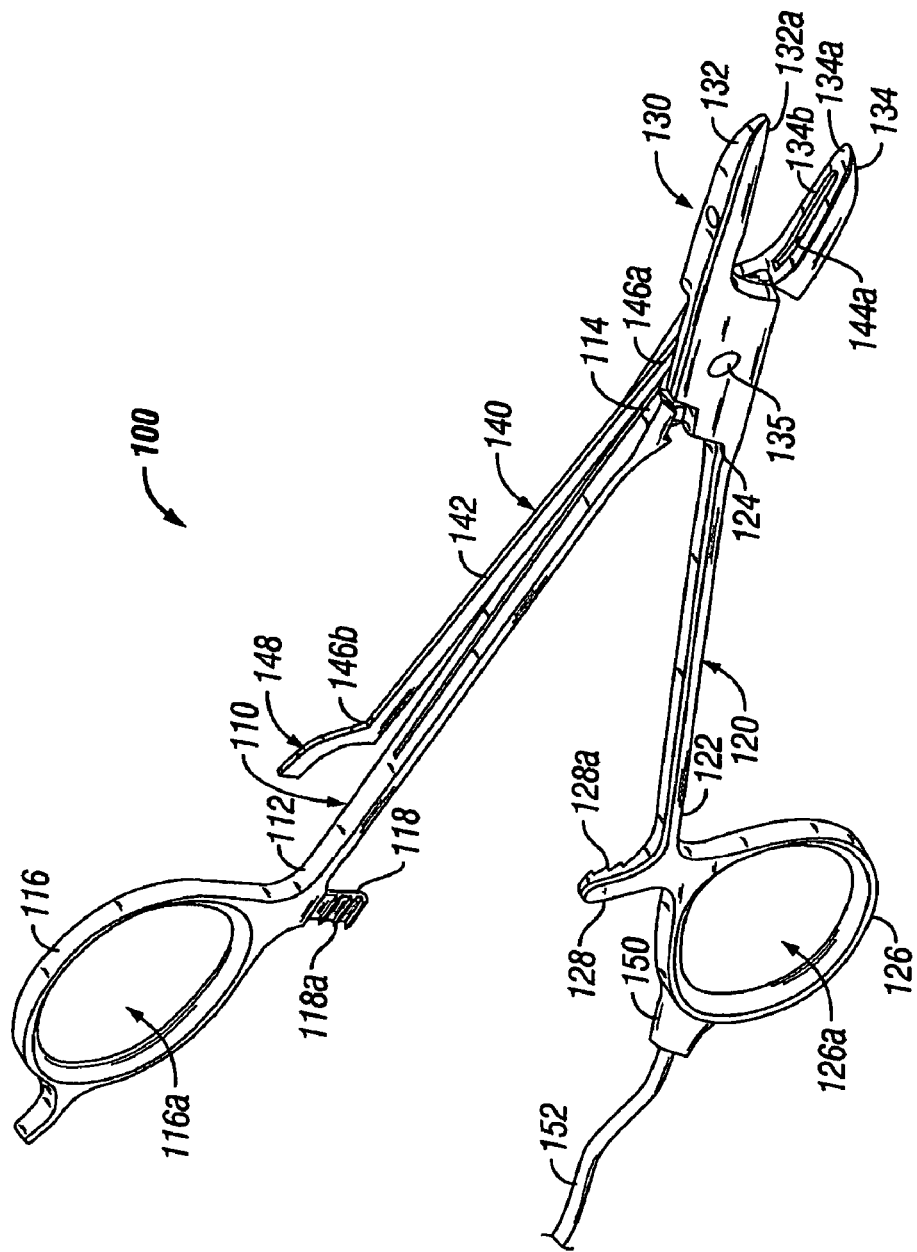
FIG. 1A is a perspective view of a forceps according to one embodiment of the present disclosure.

Referring now to FIGS. 1A-1D, a forceps or hemostat for use in open surgical procedures is generally designated as 100. Forceps 100 includes a first elongated shaft portion 110 and a second elongated shaft portion 120 each having a proximal end 112 and 122, respectively. In the drawings and in the descriptions which follow, the term "proximal", as is traditional, will refer to the end of forceps 100 which is closer to the user, while the term "distal" will refer to the end which is further from the user.

Forceps 100 includes an end effector assembly 130 which attaches to distal ends 114, 124 of shaft portions 110, 120, respectively. As explained in more detail below, end effector assembly 130 includes a pair of opposing jaw members 132, 134 which are pivotably connected about a pivot pin 135 and which are movable relative to one another to grasp tissue therebetween.

Each shaft portion 110 and 120 includes a handle 116, 126, respectively, disposed at proximal ends 112, 122, thereof. Each handle 116, 126 defines a finger hole 116a, 126a, respectively, therethrough for receiving a finger of the user. As can be appreciated, finger holes 116a, 126a, facilitate movement of shaft portions 110 and 120 relative to one another which, in turn, pivot the jaw members 132 and 134, about pivot pin 135, from an open position wherein the jaw members 132 and 134 are disposed in spaced relation relative to one another to a clamping or closed position wherein jaw members 132 and 134 cooperate to grasp tissue therebetween.

Shaft portions 110, 120 are designed to transmit a particular desired force to the opposing sealing surfaces 132a, 134a of jaw members 132, 134, respectively, when clamped. In particular, since shaft portions 110, 120 effectively act together in a spring-like manner (i.e., bending that behaves like a spring), the length, width, height and deflection of shaft portions 110, 120 will directly effect the overall transmitted force imposed on opposing jaw members 132, 134. Jaw members 132, 134 are more rigid than shaft portions 110, 120 and the strain energy stored in the shaft portions 110, 120 provides a constant closure force between jaw members 132, 134.

Each shaft portion 110, 120 also includes a ratchet portion 118, 128. Each ratchet, e.g., 118, extends from a proximal end of its respective shaft portion 110 towards the other ratchet 128 in a generally vertically aligned manner. The inner facing surfaces of each ratchet 118, 128 includes a plurality of flanges 118a, 128a, respectively, which project from the inner facing surface of each ratchet 118, 128 such that the ratchets 118, 128 can interlock in at least one position. In the embodiment shown in FIG. 1A, ratchets 118, 128 interlock at several different positions. Each ratchet position holds a specific, i.e., constant, strain energy in shaft portions 110, 120 which, in turn, transmits a specific force to jaw members 132, 134.

One of the shaft portions, e.g., shaft portion 120, includes a proximal shaft connector 150 which is designed to connect forceps 100 to a source of electrosurgical energy, e.g., an electrosurgical generator (not shown). Connector 150 electromechanically engages a conducting cable 152 such that the user may selectively apply electrosurgical energy as needed.

As briefly discussed above, jaw members 132, 134 are selectively movable about pivot pin 135 from the open position to the closed position for grasping tissue therebetween. Jaw members 132 and 134 are generally symmetrical and include similar component features which cooperate to permit facile rotation about pivot pin 135 to effect the grasping and sealing of tissue. As a result and unless otherwise noted, jaw member 132 and the operative features associated therewith are initially described herein in detail and the similar component features with respect to jaw member 134 will be briefly summarized thereafter. Moreover, many of the features of jaw members 132 and 134 are described in detail in commonly-owned U.S. patent application Ser. Nos. 10/284, 562, 10/116,824, 09/425,696, 09/178,027 and PCT Application Ser. No. PCT/US01/11420 the contents of which are all hereby incorporated by reference in their entirety herein.

Jaw member 132 includes an electrically conductive sealing surface 132a which conducts electrosurgical energy of a first potential to the tissue upon activation of forceps 100. Exemplary embodiments of conductive sealing surface 132a are discussed in commonly-owned, co-pending PCT Application Serial No. PCT/US01/11412 and commonly owned, co-pending PCT Application Serial No. PCT/US01/11411, the contents of both of these applications being incorporated by reference herein in their entirety.

Similar to jaw member 132, jaw member 134 includes an electrically conductive sealing surface 134a for conducting electrosurgical energy of a second potential to the tissue upon activation of forceps 100.

It is envisioned that one of the jaw members, e.g., 132, includes at least one stop member (not shown) disposed on the inner facing surface of the electrically conductive sealing surface 132a (and/or 134a). Alternatively or in addition, the stop member(s) may be positioned adjacent to the electrically conductive sealing surfaces 132a, 134a or proximate the pivot pin 135. The stop member(s) is/are designed to define a gap between opposing jaw members 132 and 134 during sealing. The separation distance during sealing or the gap distance is within the range of about 0.001 inches (~0.03 millimeters) to about 0.006 inches (~0.016 millimeters).

A detailed discussion of these and other envisioned stop members as well as various manufacturing and assembling processes for attaching, disposing, depositing and/or affixing the stop members to the electrically conductive sealing surfaces 132a, 134a are described in commonly-assigned, co-pending PCT Application Serial No. PCT/US01/11222 and U.S. application Ser. No. 10/471,818 which are both hereby incorporated by reference in their entirety herein.

As mentioned above, two mechanical factors play an important role in determining the resulting thickness of the sealed tissue and effectiveness of the seal, i.e., the pressure applied between opposing jaw members 132 and 134 and the size of the gap between opposing jaw members 132 and 134 (or opposing sealing surface 132a and 134a during activation). It is known that the thickness of the resulting tissue seal cannot be adequately controlled by force alone. In other words, too much force and jaw members 132 and 134 may touch and possibly short resulting in little energy traveling through the tissue thus resulting in an inadequate seal. Too little force and the seal would be too thick. Applying the correct force is also important for other reasons: to oppose the walls of the vessel; to reduce the tissue impedance to a low enough value that allows enough current through the tissue; and to overcome the forces of expansion during tissue heating in addition to contributing towards creating the required end tissue thickness which is an indication of a good seal.

Sealing surfaces 132a and 134a are relatively flat to avoid current concentrations at sharp edges and to avoid arcing between high points. In addition, and due to the reaction force of the tissue when engaged, jaw members 132 and 134 are manufactured to resist bending, i.e., tapered along their length to provide a constant pressure for a constant tissue thickness at parallel and the thicker proximal portion of jaw members 132 and 134 will resist bending due to the reaction force of the tissue.

As best shown in FIGS. 1A-1D, forceps 100 further includes a cutting mechanism 140 operatively associated therewith. Cutting mechanism 140 includes an arm portion 142 pivotably connected to one of the first and second shaft portions 110, 120, a cutting element 144 (e.g., blade, knife, scalpel, etc.) disposed at a distal end 146a thereof, and a finger gripping element 148 disposed at a proximal end 146b thereof.

Cutting mechanism 140 is pivotably coupled to shaft portion 110 about pivot pin 135. Cutting mechanism 140 is pivotably coupled to shaft portion 110 in such a manner that cutting element 144 is biased (via a spring or the like) in a retracted position within a slot 134b defined in sealing surface 134a of jaw member 134. Cutting mechanism 140 is selectively movable about pivot pin 135 to deploy cutting element 144 from within slot 134b to cut tissue. Cutting element 144 may also be movably retractable depending upon a particular purpose.

In particular, cutting mechanism 140 is pivotable from a first position in which cutting element 144 is retained at least substantially within slot 134b of jaw member 134 to a second position in which cutting element 144 is deployed from jaw member 134. When cutting element 144 is disposed in jaw member 134, arm portion 142 of cutting assembly 142 is spaced a distance from shaft portion 110.

Figure 1B:
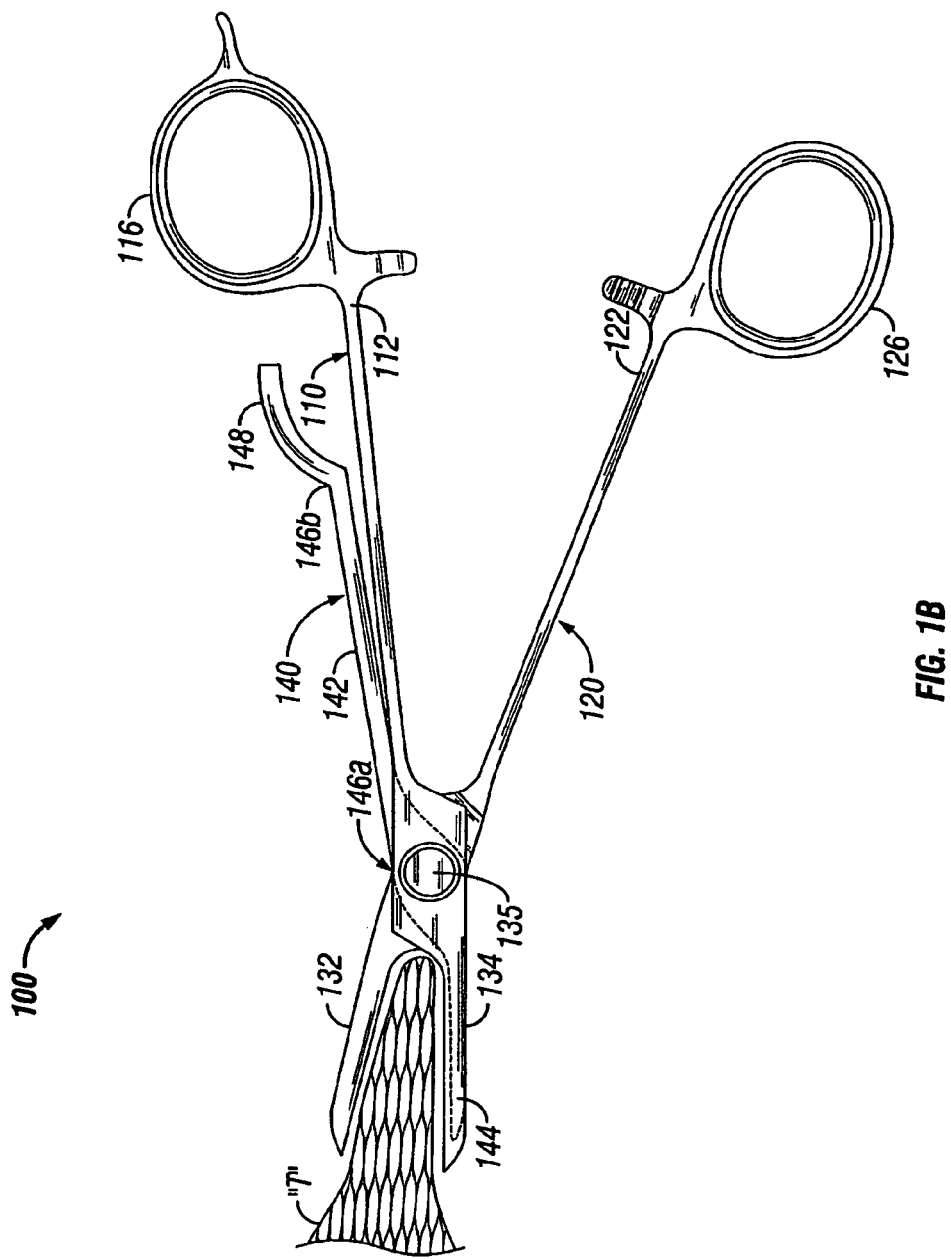
FIG. 1B is a side, elevational view of the forceps of FIG. 1A shown in an open position.
Figure 1C:
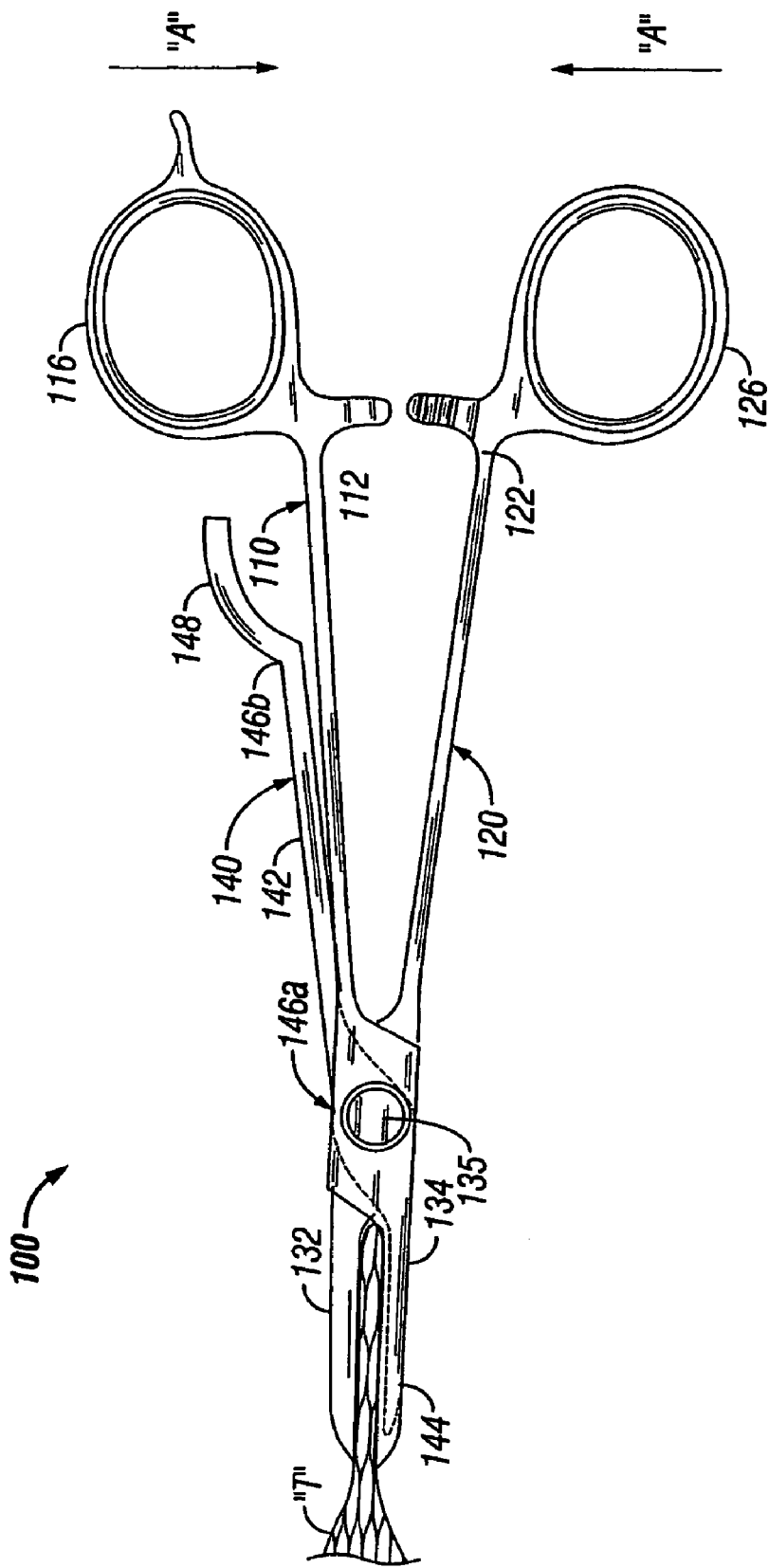
FIG. 1C is a side, elevational view of the forceps of FIGS. 1A and 1B shown in a closed position and the cutting assembly shown in an unactuated position.
Figure 1D:
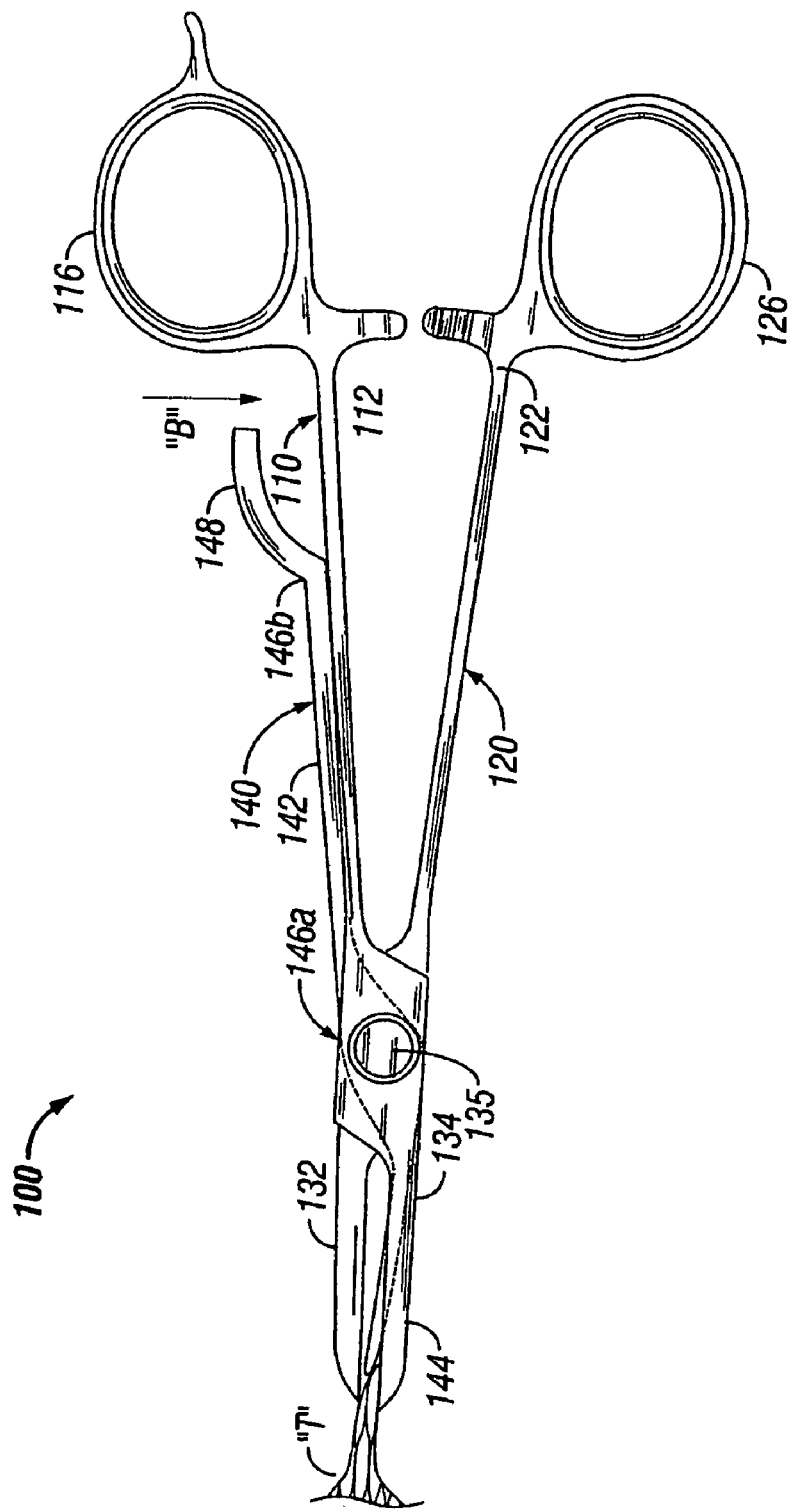
FIG. 1D is a side, elevational view of the forceps of FIGS. 1A-1C shown in a closed position and the cutting assembly shown in an actuated position.

With reference to FIGS. 1B-1D, a method of using forceps 100 will now be described in detail. As seen in FIG. 1B, with shaft portions 110, 120 in the open position, such that jaw members 132, 134 are spaced from one another, and with cutting assembly 140 in the first position (i.e., within slot 134b), jaw members 132, 134 are maneuvered around the target tissue "T". As seen in FIG. 1C, following manipulation and positioning of jaw members 132, 134 about target tissue "T", forceps 100 is moved from the open position to the closed position. In particular, proximal ends 112, 122 of shaft portions 110 and 120 are moved toward one another, in the direction of arrows "A", to thereby proximate jaw members 132, 134 toward one another.

In so doing, target tissue "T" is clamped or grasped between jaw members 132, 134. Desirably, the user then activates a hand switch or a foot switch (not shown) to provide electrosurgical energy to each jaw member 132, 134 to communicate energy through target tissue "T" held therebetween to effect a tissue seal. Once target tissue "T" is sealed, as seen in FIG. 1D, cutting mechanism 140 is actuated, e.g., arm portion 142 is moved toward shaft portion 110 in the direction of arrow "B", to sever target tissue "T" along the tissue seal. In particular, upon movement of arm portion 142 cutting element 144 pivots about pivot pin 135 and deploys from jaw member 134 toward jaw member 132 to thereby slice, cut and/or otherwise divide target tissue "T" along the previously formed tissue seal.

Figure 2A:
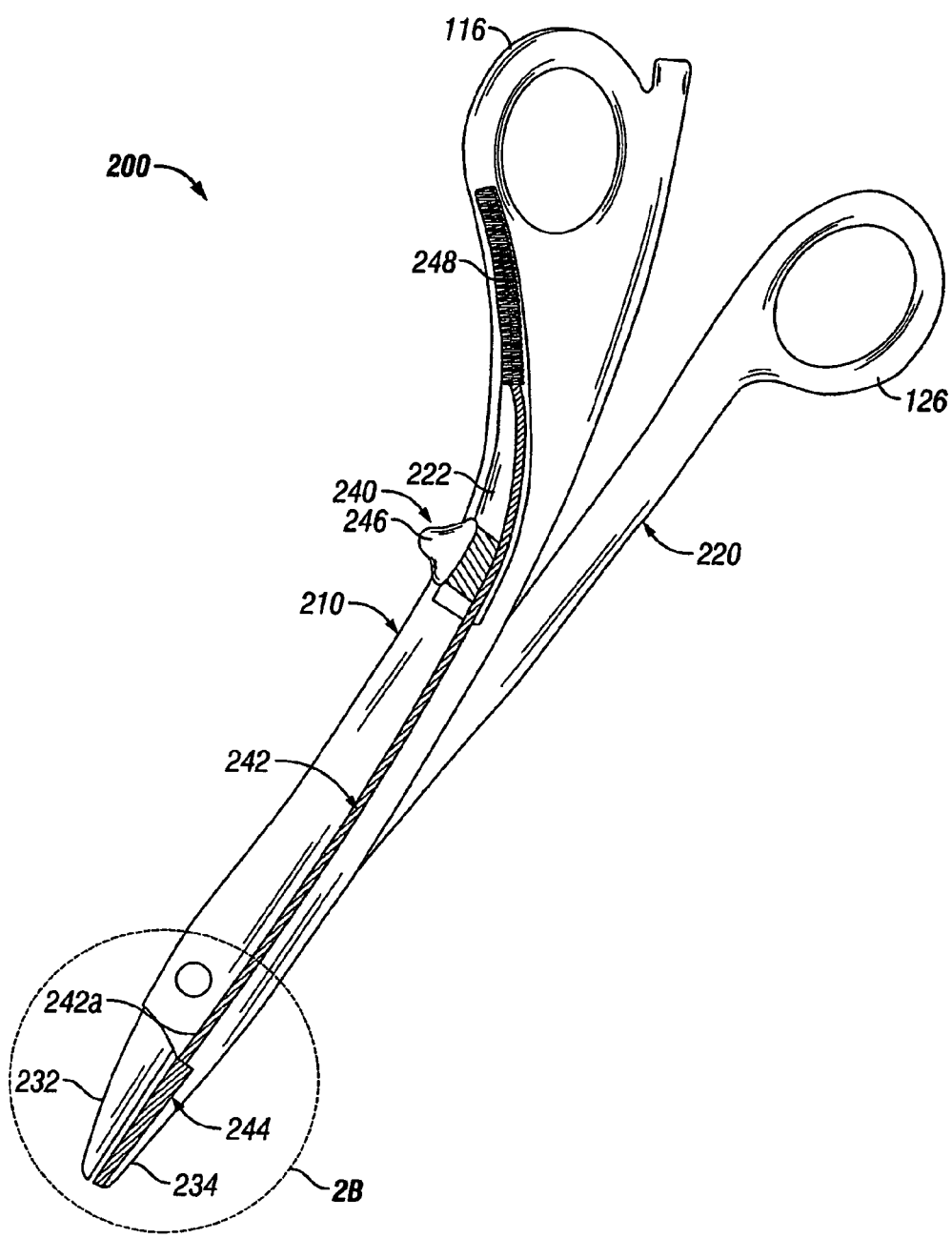
FIG. 2A is a cross-sectional, side elevational view of an alternate embodiment of a forceps according to the present disclosure.
Figure 2B:
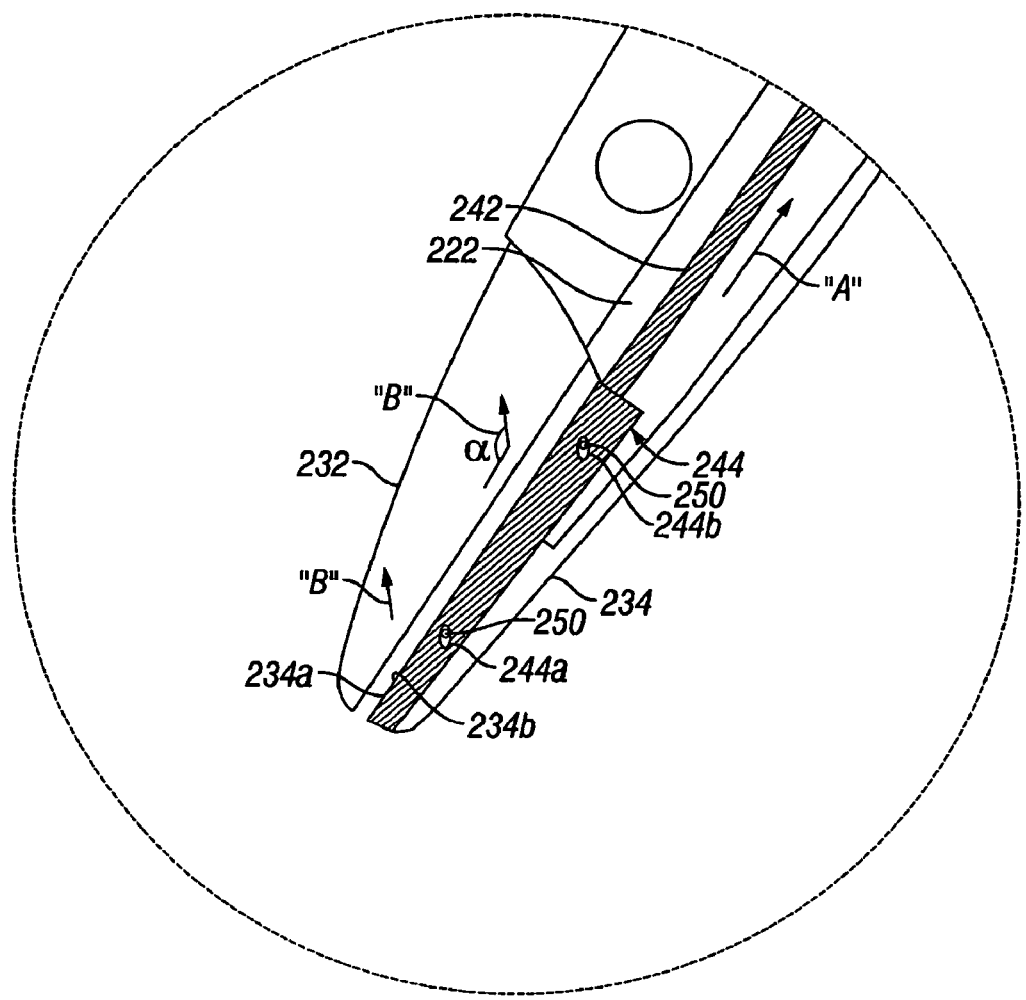
FIG. 2B is an enlarged view of the indicated area of detail of FIG. 2A, illustrating a cutting element of the forceps in a first position.
Figure 2C:
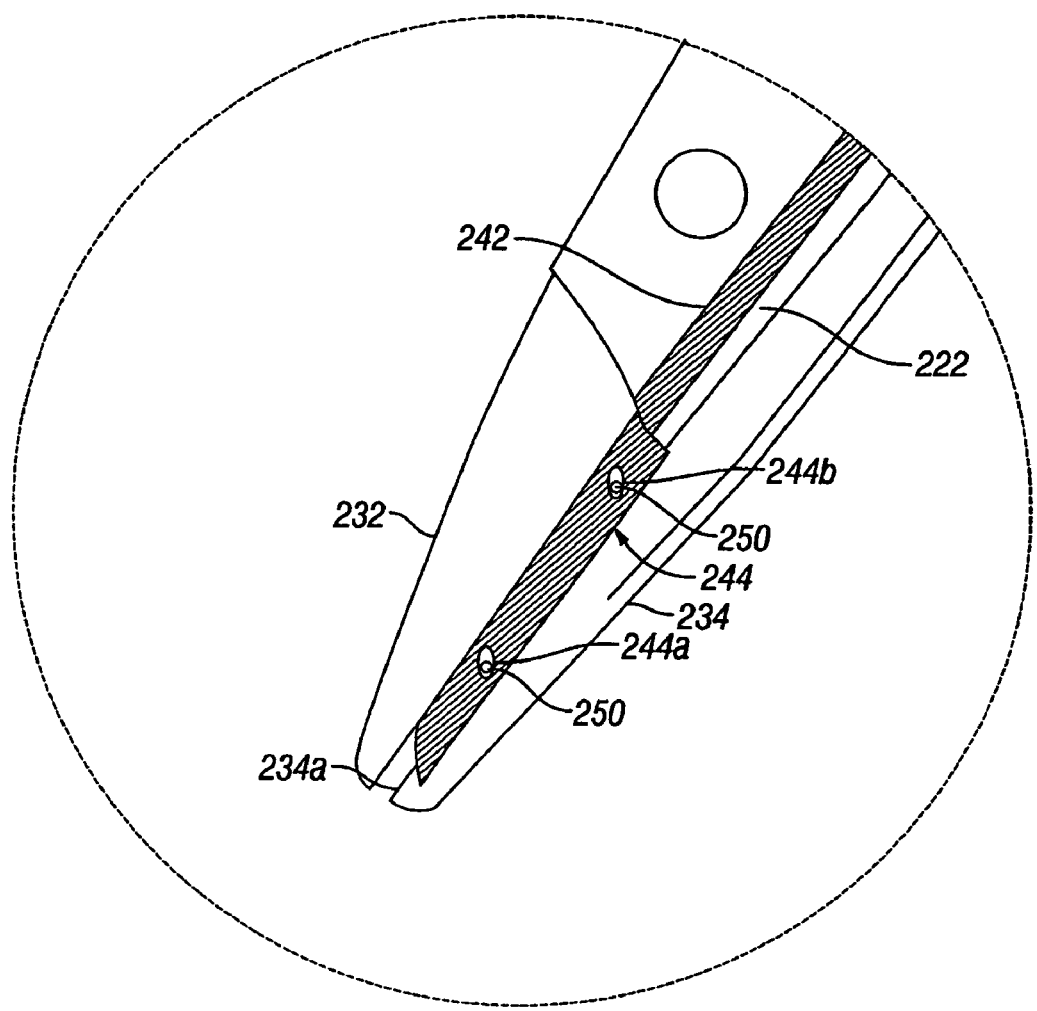
FIG. 2C is an enlarged view of the indicated area of detail of FIG. 2A, illustrating the cutting element of the forceps in a second position.

Turing now to FIGS. 2A-2C, a forceps in accordance with another embodiment of the present disclosure is shown generally as 200. Forceps 200 is similar to forceps 100 and will only be described in detail to the extent necessary to identify differences in construction and operation.

Forceps 200 includes a cutting mechanism 240 operatively associated therewith. Cutting mechanism 240 includes a drive rod 242 for advancing cutting mechanism 240 through shaft portion 210, which will be explained in greater detail below. Drive rod 242 includes a distal end 242a configured to mechanically support a cutting element 244. Cutting element 244 is disposed in slot 234b formed in seal surface 234a of jaw member 234 (see FIG. 2B). Cutting mechanism 240 further includes a finger tab 246 operatively associated with drive rod 242 such that movement of finger tab 246 moves drive rod 242 in the corresponding direction.

Shaft portion 210 includes at least one guide channel 222 formed therein for controlling and/or guiding drive rod 242 through movement therethrough. Drive rod 242 is made from a flexible wire or plastic sheath which does not buckle upon movement thereof.

A spring 248 may be employed within guide channel 222 to bias cutting mechanism 240 back to the unactuated position upon proximal movement of tab 246 such that upon release of finger tab 246, the force of spring 248 automatically returns cutting mechanism 240 to its distal-most position within guide channel 222 which, in turn, retracts cutting element 244 within slot 234. While a spring 248 is shown for maintaining cutting mechanism 240 in a distal-most position, it is envisioned and within the scope of the present disclosure that a spring, e.g., a coil spring, (not shown) can be operatively associated therewith for maintaining cutting mechanism 240 in a proximal-most position and wherein finger tab 246 is positioned so as to drive cutting mechanism 240 in a distal direction.

As best seen in FIGS. 2B and 2C, cutting element 244 is provided with at least one elongated slot, preferably a pair of elongated slots 244a, 244b, formed therein. Slots 244a, 244b are oriented at an angle with respect to the longitudinal axis of forceps 200. The portion of slots 244a, 244b which is closest to seal surface 234a of jaw member 234 is located proximal of the portion of slots 244a, 244b which is furthest from seal surface 234a of jaw member 234.

A pin 250 is provided within each slot 244a, 244b. Each pin 250 is fixedly positioned relative to jaw member 234. When cutting element 244 is in a distal-most position, pins 250 are located in the portion of slots 244a, 244b closest to seal surface 234a.

Figure 2D:
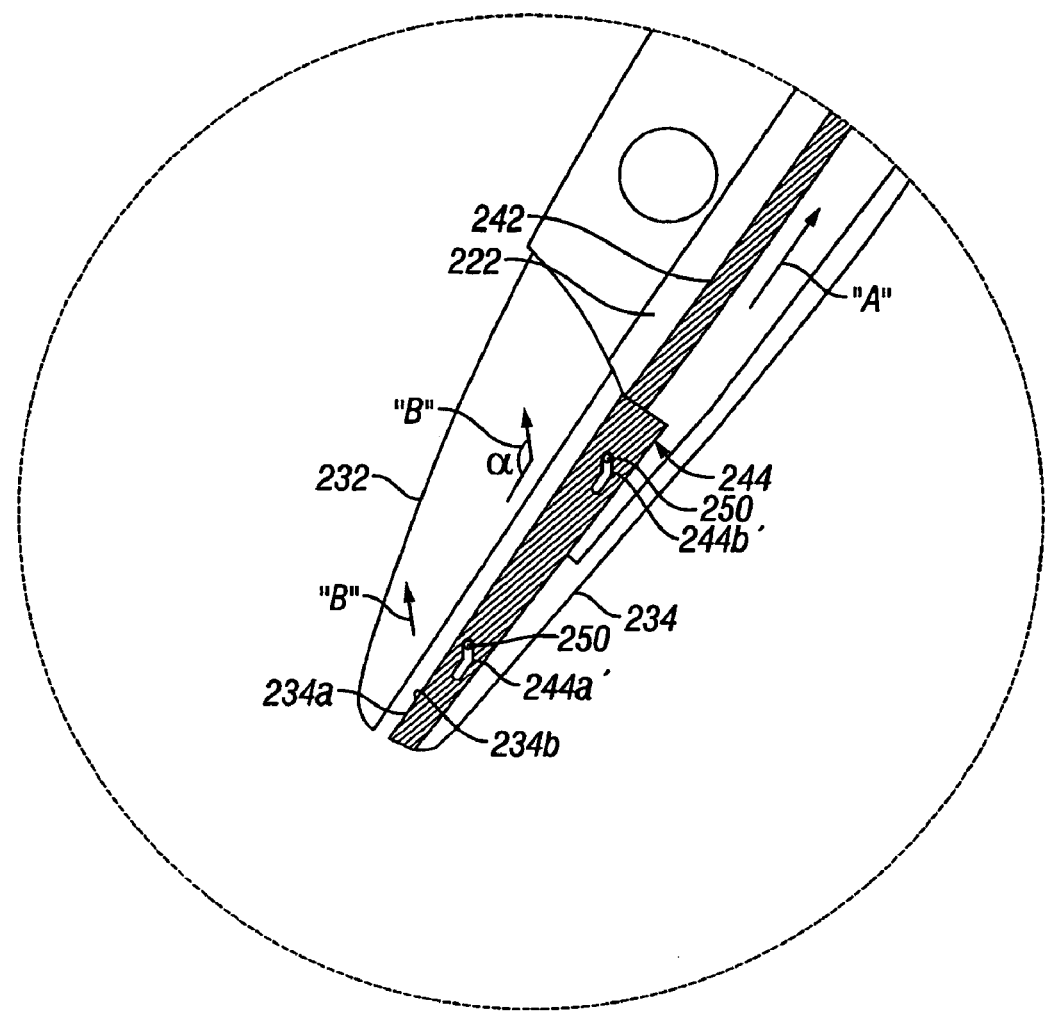
FIG. 2D is an enlarged view of the indicated area of detail of FIG. 2A, illustrating a cutting element of the forceps according to an alternate embodiment of the disclosure.

As seen in FIGS. 2B and 2C, in operation and following application of electrosurgical energy to jaw members 232, 234, to thereby seal the target tissue held therebetween, the user activates finger tab 246 to thereby urge drive rod 242 in a proximal direction, as indicated by arrow "A". In so doing, cutting element 244 is urged in an angular direction relative to the longitudinal axis, as indicated by arrows "B". In particular, cutting element 244 is drawn both proximally and toward jaw member 232 (i.e., deployed from slot 234b formed in sealing surface 234a of jaw member 234, to thereby slice the target tissue which is clamped between jaw members 232, 234. In other words, cutting element 244 is drawn in direction "B" by the camming action created between slots 244a, 244b and pins 250. While cam slots 244a, 244b may be diagonal, as seen in FIG. 2D, cutting element 244 may be provided with cam slots 244a' and 244b' having a diagonal portion and a longitudinally extending portion integrally connected to the diagonal portion to thereby by create a slicing or cutting motion for cutting element 244.

Following the cutting of the target tissue, finger tab 246 may be released to thereby allow the force of spring 248 to automatically return cutting mechanism 240 to its distal-most position within guide channel 222 for subsequent sealing and cutting, which, as mentioned above, retract cutting element 244 to within slot 234b.

Turing now to FIGS. 3A-3D, a forceps 300, having a distal end in accordance with another embodiment of the present disclosure, is shown. Forceps 300 is similar to forceps 100 and 200 and will only be described in detail to the extent necessary to identify differences in construction and operation.

Forceps 300 includes a cutting mechanism 340 operatively associated therewith. Cutting mechanism 340 includes a cutting element 344 disposed in slot 334b formed in sealing surface 334a of jaw member 334. Cutting element 344 includes a camming surface 346 at a rear portion thereof, i.e., which extends outwardly from a side opposite sealing surface 334a of jaw member 334.

Cutting element 344 is pivotably supported in slot 334b by a pivot pin 350. A biasing member 348, e.g., a torsion spring or the like, may be employed within jaw member 334 to bias cutting element 344 in a retracted, i.e., undeployed, condition. Upon at least partial deployment of cutting element 344, biasing member 348 is biased such that upon release of cutting element 344, the force of the biasing member 348 automatically returns cutting element 344 into jaw member 334. Cutting mechanism 340 further includes an advancing sheath 342 operatively associated with forceps 300 for deploying cutting element 344. Any type of known actuation may be employed to advance sheath 342.

Figure 3A:
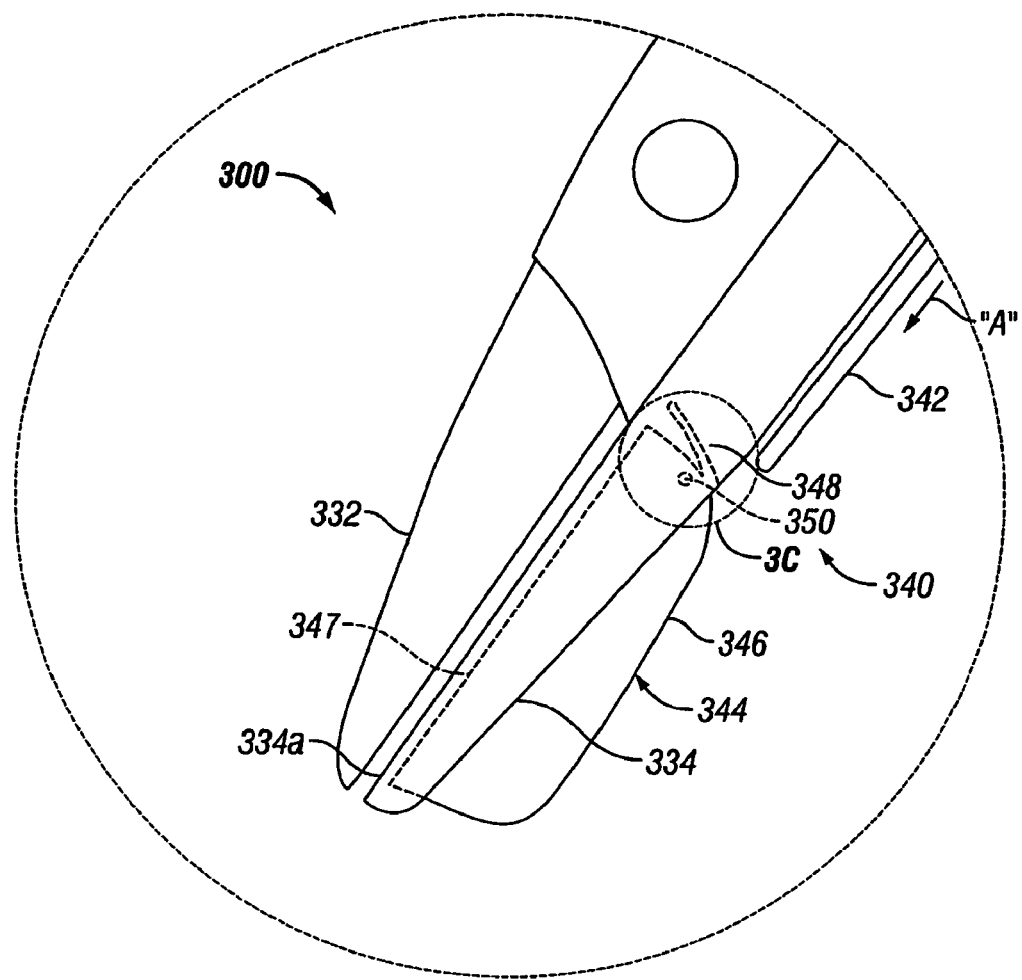
FIG. 3A is an enlarged, schematic side elevational view of a distal end of a forceps constructed according to another embodiment of the present disclosure, illustrating a cutting assembly in a first position.
Figure 3B:
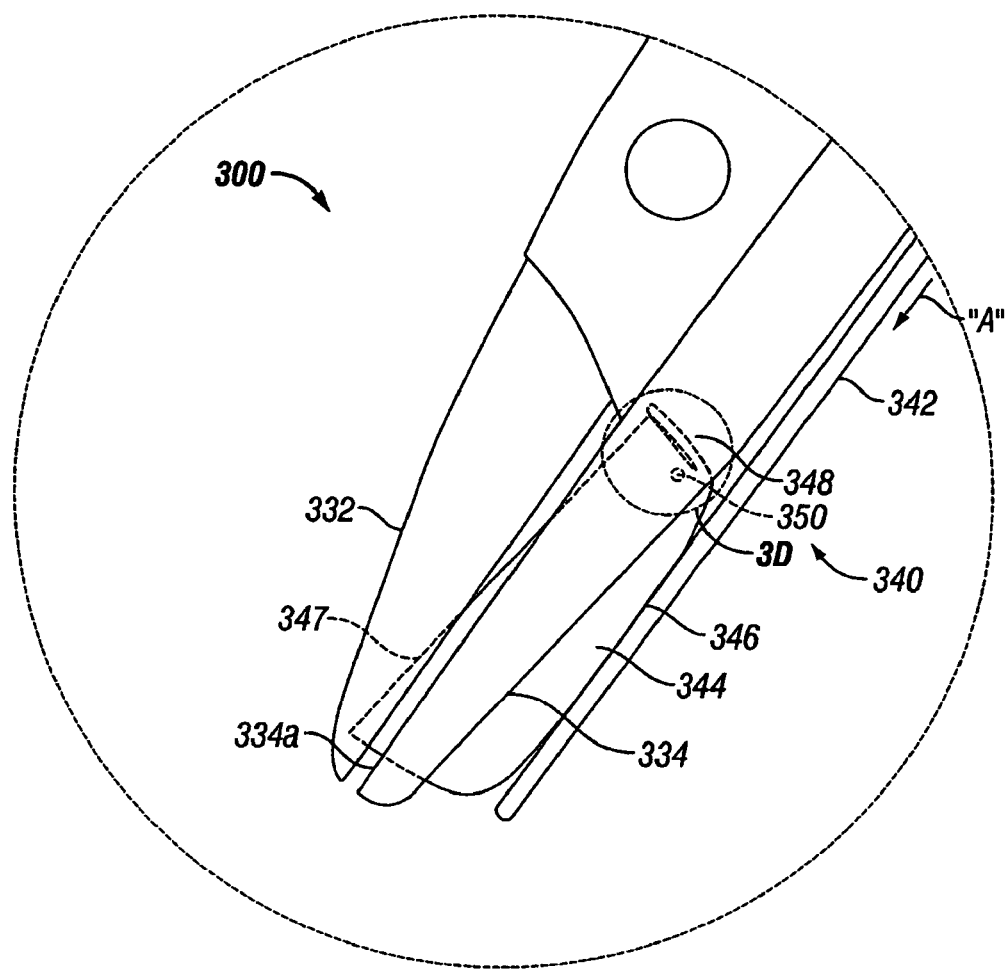
FIG. 3B is an enlarged, schematic side elevational view of the distal end of the forceps of FIG. 3A, illustrating the cutting assembly in a second position.

As seen in FIGS. 3A and 3B, following application of electrosurgical energy to jaw members 132, 134 to seal tissue held therebetween, the user advances sheath 342 a distal direction, as indicated by arrow "A", to engage camming surface 346 of cutting element 344 and urge cutting element 344 out of slot 334b in the direction of arrow "B" to sever tissue. Following the cutting of the tissue, sheath 342 is withdrawn in a proximal direction until camming surface 346 of cutting element 344 is disengaged. The force of biasing member 348 automatically returns cutting mechanism 340 into slot 334b of jaw member 334.

Figure 3C:
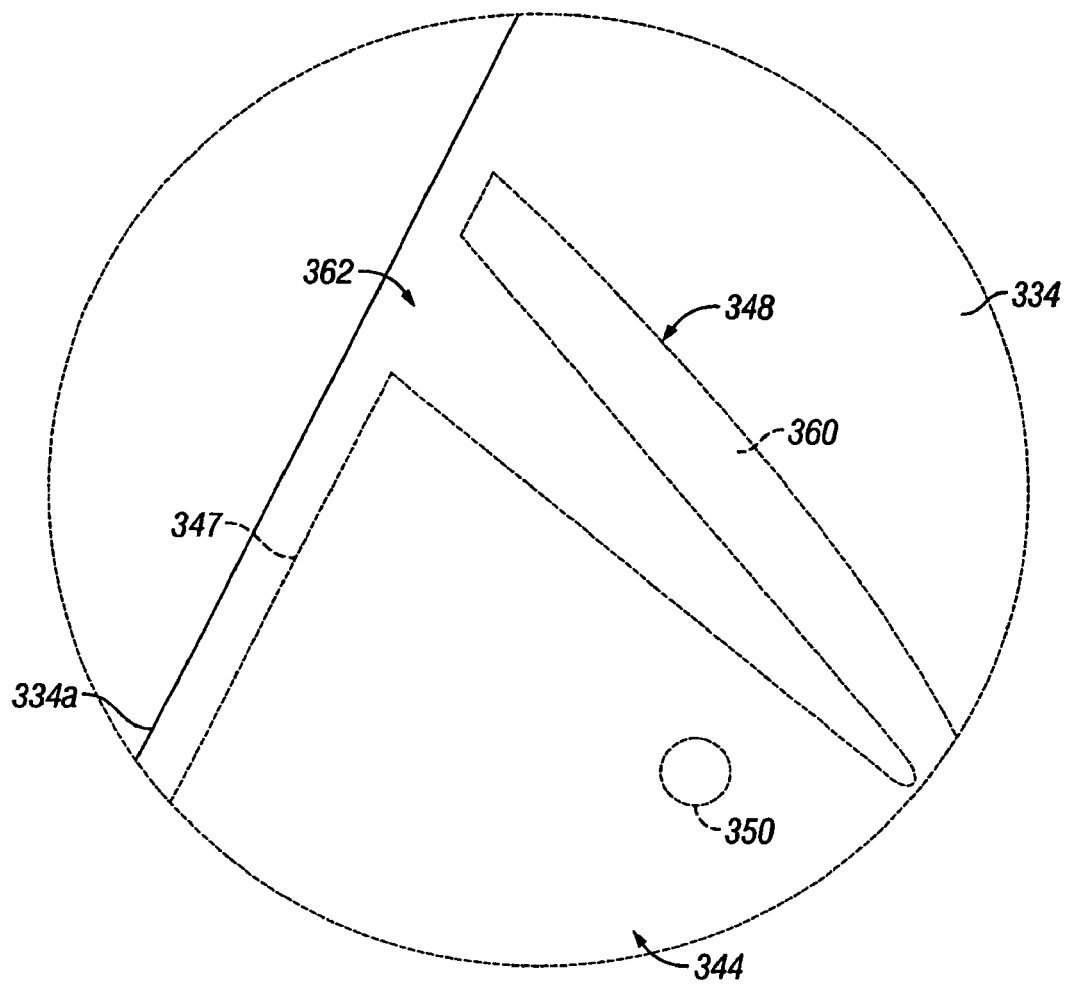
FIG. 3C is an enlarged, schematic view of an alternate biasing arrangement for the cutting assembly shown in a first position.
Figure 3D:
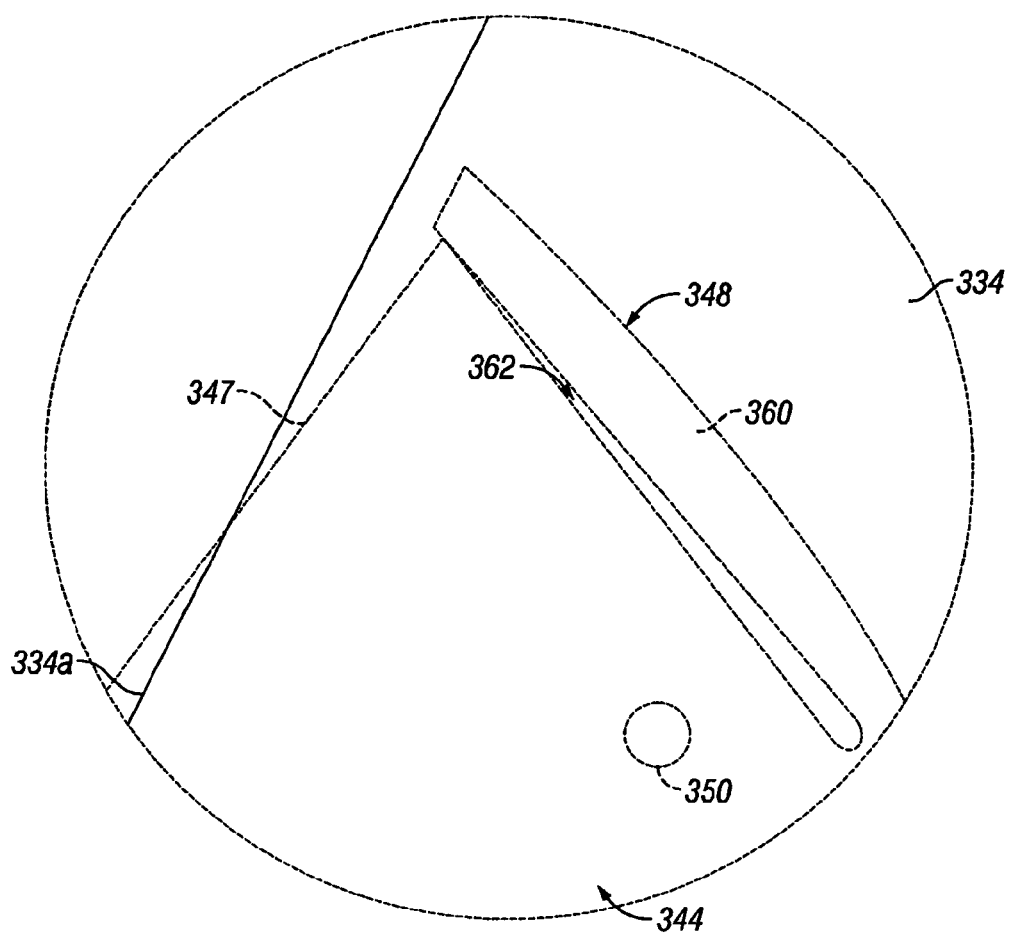
FIG. 3D is an enlarged, schematic view of an alternate biasing arrangement of FIG. 3C in a second position.

Turning now to FIGS. 3C and 3D, a detailed discussion of biasing member 348 is provided. As seen in FIG. 3C, cutting element 344 includes a rear flange or arm 360 which defines a notch 362 formed between a proximal end of cutting element 344 and arm 360. Notch 362 is located proximal of pin 350. Notch 362 extends through cutting edge 347 of cutting element 344. Cutting element 344 is fabricated from spring type steel or any other material exhibiting resilient characteristics.

In operation, as seen in FIGS. 3C and 3D, as cutting element 344 is urged out of slot 334b of jaw member 334, in the direction of arrow "B" (FIG. 3B), notch 362 closes against the bias created by arm 360. Following the cutting of the target tissue, sheath 342 is withdrawn in a proximal direction until camming surface 346 of cutting element 344 is disengaged. The biasing force created by arm 360 automatically returns cutting mechanism 340 into slot 334b of jaw member 334.

Figure 4A:
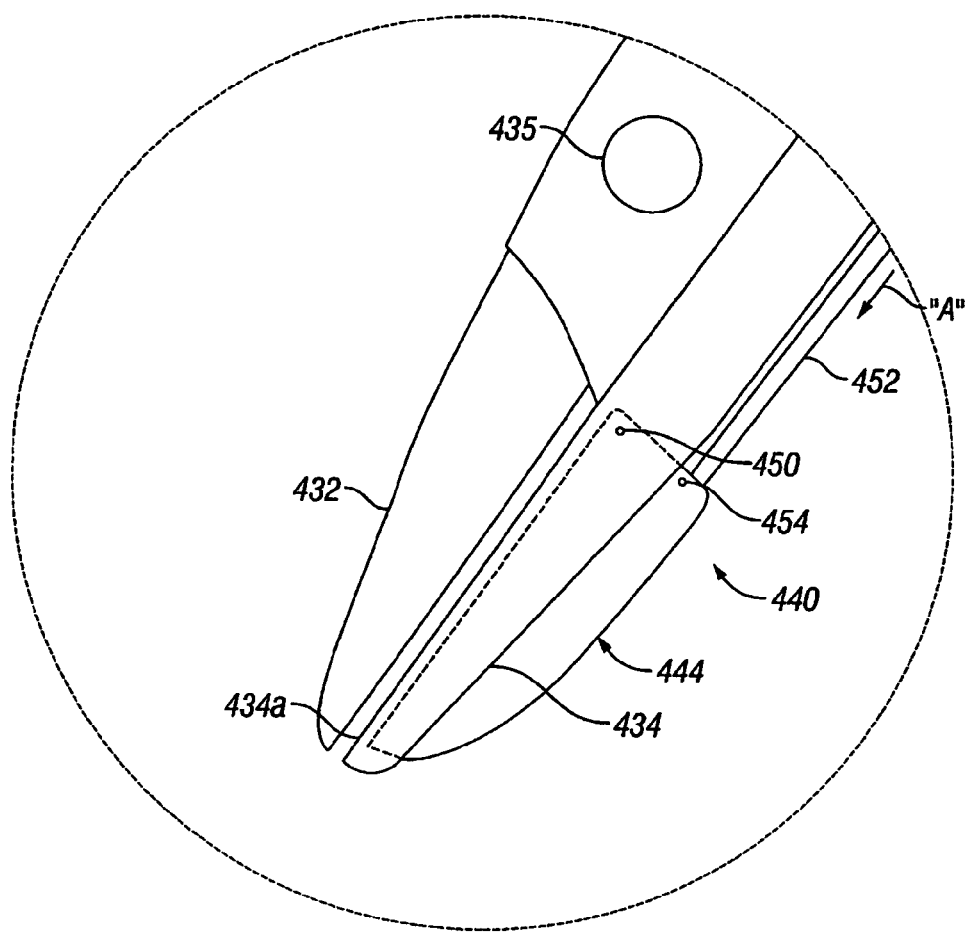
FIG. 4A is an enlarged schematic side elevational view of a distal end of a forceps constructed according to yet another embodiment of the present disclosure, illustrating a cutting assembly in a first position.
Figure 4B:
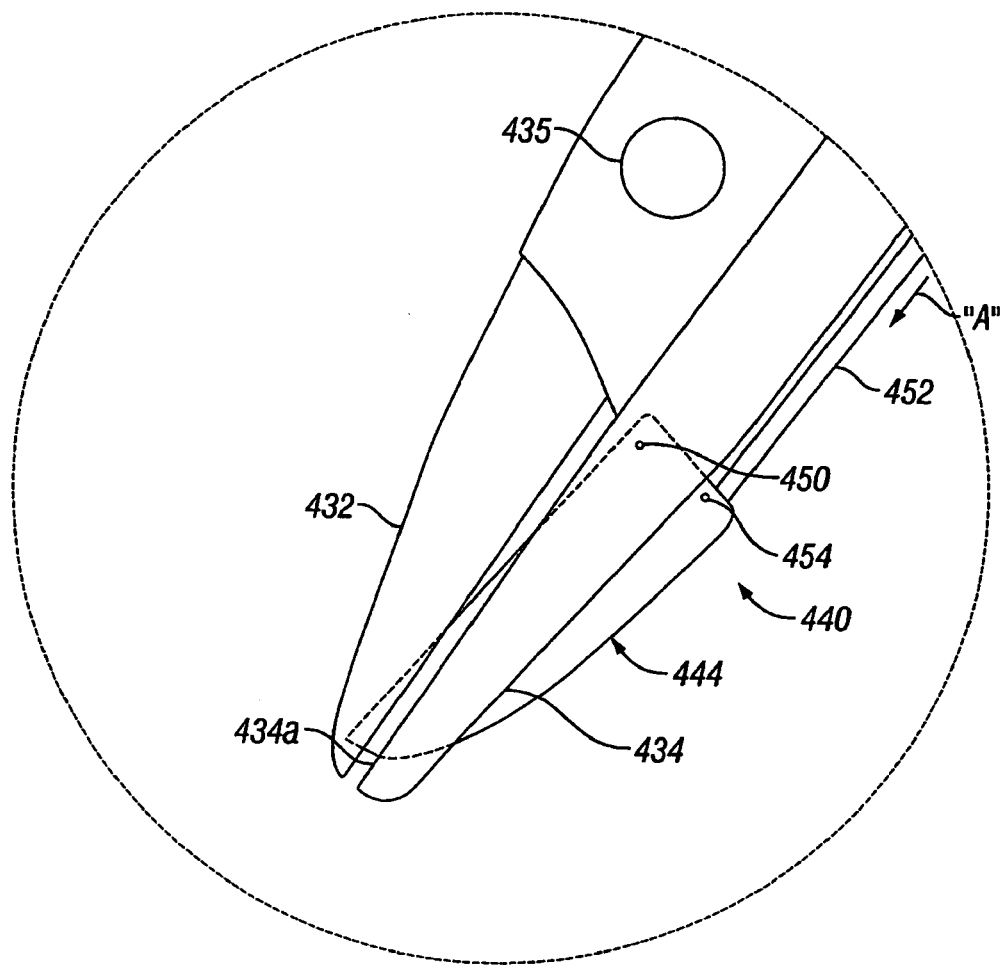
FIG. 4B is an enlarged schematic side elevational view of the distal end of the forceps of FIG. 4A, illustrating the cutting assembly in a second position.

Turning now to FIGS. 4A and 4B an alternative embodiment includes a cutting element 444 is pivotably connected to a drive rod 452 by a pin 454. In this manner, as drive rod 452 is driven in a distal direction, as indicated by arrow "A", cutting element 444 is pivoted about pin 450 and urged out of slot 334b of jaw member 334. Following the cutting step, drive rod 452 is withdrawn in a proximal direction to urge cutting element 444 back into jaw member 334.

It is envisioned and within the scope of the present disclosure that a biasing member, e.g., a spring, (not shown) may be provided for returning cutting element 444 into jaw member 334 following deployment by drive rod 452.

It is further envisioned and within the scope of the present disclosure to provide a cutting element 444 configured such that cutting element 444 is pivotable about pivot pin 435.

It is envisioned that any of the cutting elements disclosed herein may be fabricated from plastic and/or metal (e.g., stainless steel, titanium, etc.). Desirably, the cutting elements are fabricated from non-conductive materials to thereby reduce the potential for stray currents and/or shorting.

From the foregoing and with reference to the various figure drawings, those skilled in the art will appreciate that certain modifications can also be made to the present disclosure without departing from the scope of the same. For example, none of the aforedescribed forceps require that the tissue be necessarily cut after sealing or that the tissue be sealed prior to cutting. As can be appreciated, this gives the user additional flexibility when using the instrument.

For example, it is also contemplated that forceps 100, 200 and/or 300 (and/or the electrosurgical generator used in connection therewith) may include a sensor or feedback mechanism (not shown) which automatically selects the appropriate amount of electrosurgical energy to effectively seal the particularly-sized tissue grasped between the jaw members. The sensor or feedback mechanism may also measure the impedance across the tissue during sealing and provide an indicator (visual and/or audible) that an effective seal has been created between jaw members 132 and 134. Commonly-owned U.S. patent application Ser. No. 10/073,761, filed on Feb. 11, 2002, entitled "Vessel Sealing System"; U.S. patent application Ser. No. 10/626,390, filed on Jul. 24, 2003, entitled "Vessel Sealing System"; U.S. patent application Ser. No. 10/427,832, filed on May 1, 2003, entitled "Method and System for Controlling Output of RF Medical Generator"; U.S. patent application Ser. No. 10/761,524, filed on Jan. 21, 2004, entitled "Vessel Sealing System"; U.S. Provisional Application No. 60/539,804, filed on Jan. 27, 2004, entitled "Method of Tissue Fusion of Soft Tissue by Controlling ES Output Along Optimal Impedance Curve"; U.S. Provisional Application No. 60/466,954; filed on May 1, 2003, entitled "Method and System for Programming and Controlling an Electrosurgical Generator System"; and U.S. Pat. No. 6,398,779, disclose several different types of sensory feedback mechanisms and algorithms which may be utilized for this purpose. The contents of these applications are hereby incorporated by reference herein.

Experimental results suggest that the magnitude of pressure exerted on the tissue by the sealing surfaces of jaw members 132 and 134 are important in assuring a proper surgical outcome. Tissue pressures within a working range of about 3 $kg/cm^2$ to about 16 $kg/cm^2$ and, desirably, within a working range of 7 $kg/cm^2$ to 13 $kg/cm^2$ have been shown to be effective for sealing arteries and vascular bundles. Tissue pressures within the range of about 4 $kg/cm^2$ to about 6.5 $kg/cm^2$ have proven to be particularly effective in sealing arteries and particular tissue bundles.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. An open electrosurgical forceps for sealing tissue, comprising:

first and second shaft portions pivotably associated with one another, each shaft portion having a jaw member disposed at a distal end thereof, the jaw members being movable from a first position in spaced relation relative to one another to at least one subsequent position wherein the jaw members cooperate to grasp tissue therebetween, each of the jaw members including an electrically conductive sealing surface being configured to communicate electrosurgical energy through tissue held therebetween, at least one of the jaw members including a slot formed through the sealing surface thereof;

a cutting mechanism operatively associated with the first and second jaw members, the cutting mechanism including:
  a cutting element disposed within the slot of the at least one jaw member, the cutting element being movable about a pivot from a first position wherein the cutting element is retracted within the at least one jaw member and a second position in which a cutting edge of the cutting element at least partially projects from a sealing surface of the at least one jaw member, the cutting element including a biasing member at a proximal end thereof, the biasing member operably disposed within the jaw member and configured for biasing the cutting element toward the first position and pivoting the cutting element, the biasing member including a notched portion configured to facilitate pivoting the cutting element between the first and second positions, the notched portion disposed proximal relative to the pivot and extending to the cutting edge of the cutting element; and
  an actuator operatively associated with the cutting element which upon movement thereof selectively advances the cutting element from the first position to the second position.

2. The open electrosurgical forceps according to claim 1, wherein the cutting element is pivotably disposed within the slot of the jaw member.

3. The open electrosurgical forceps according to claim 1, wherein the cutting element extends out through the jaw member and defines a camming surface.

4. The open electrosurgical forceps according to claim 3, wherein the second shaft portion reciprocably supports the actuator, the actuator being movable from a first position spaced from the cutting element to a second position in contact with the cutting element.

5. The open electrosurgical forceps according to claim 4, wherein upon displacement of the actuator from the first position to the second position, the actuator engages the camming surface of the cutting element and urges the cutting element from the first position to the second position.

6. The open electrosurgical forceps according to claim 1, wherein the biasing member located at the proximal end of the cutting element is a torsion spring.

7. The open electrosurgical forceps according to claim 4, wherein movement of the actuator pivots the cutting element between the first and second positions.

8. An open electrosurgical forceps for sealing tissue, comprising:
  a pair of shaft portions pivotably coupled to one another at a first pivot, each shaft portion including a jaw member at a distal end thereof for grasping tissue therebetween, each jaw member including a sealing surface adapted to conduct electrosurgical energy through tissue grasped therebetween and one of the sealing surfaces includes a slot defined therein;
  a cutting mechanism operatively coupled to at least one of the pair of shaft portions, the cutting mechanism comprising:
  a cutting element pivotably coupled to at least one of the jaw members and configured to pivot within the slot, the cutting mechanism being selectively moveable about a second pivot from a first position in which the cutting element is retracted within the slot and a second position in which a cutting edge of the cutting element at least partially projects from the slot to cut tissue disposed between the jaw members;
  a biasing member operably disposed on the cutting element and within the jaw member, the biasing member configured for biasing the cutting element toward the first position and pivoting the cutting element about the second pivot, the biasing member including a notched portion configured to facilitate pivoting the cutting element between the first and second positions about the second pivot, the notched portion disposed proximal relative to the second pivot and extending to the cutting edge of the cutting element; and
  an actuator operatively associated with the cutting element that, upon movement thereof, selectively pivots the cutting element from the first position to the second position,
  wherein the cutting element pivots with respect to the actuator.

9. The open electrosurgical forceps according to claim 8, wherein the actuator is integrally associated with the cutting element.

10. The open electrosurgical forceps according to claim 8, wherein the actuator is pivotably coupled to the cutting element.

11. The open electrosurgical forceps according to claim 8, wherein the actuator is spaced a distance from a first shaft portion.

12. The open electrosurgical forceps according to claim 8, wherein the actuator selectively activates the cutting element when moved relative to a first shaft portion.

13. The open electrosurgical forceps according to claim 8, wherein the actuator is a drive rod.

* * * * *